United States Patent
Yadav et al.

(10) Patent No.: US 7,306,822 B2
(45) Date of Patent: Dec. 11, 2007

(54) PRODUCTS COMPRISING NANO-PRECISION ENGINEERED ELECTRONIC COMPONENTS

(75) Inventors: Tapesh Yadav, Tucson, AZ (US); Hongxing Hu, Tucson, AZ (US)

(73) Assignee: NanoProducts Corporation, Longmont, CO (US)

( * ) Notice: Subject to any disclaimer, the term of this patent is extended or adjusted under 35 U.S.C. 154(b) by 315 days.

(21) Appl. No.: 10/854,446

(22) Filed: May 26, 2004

(65) Prior Publication Data

US 2004/0218345 A1 Nov. 4, 2004

Related U.S. Application Data

(63) Continuation of application No. 10/614,845, filed on Jul. 8, 2003, now Pat. No. 7,081,267, which is a continuation of application No. 09/988,901, filed on Nov. 19, 2001, now Pat. No. 6,610,355, which is a continuation of application No. 08/251,313, filed on Feb. 17, 1999, now Pat. No. 6,387,560, which is a continuation of application No. 08/739,257, filed on Oct. 30, 1996, now Pat. No. 5,905,000, which is a continuation-in-part of application No. 08/730,661, filed on Oct. 11, 1996, now Pat. No. 5,952,040, which is a continuation-in-part of application No. 08/706,819, filed on Sep. 3, 1996, now Pat. No. 5,851,507, and a continuation-in-part of application No. 08/707,341, filed on Sep. 3, 1996, now Pat. No. 5,788,738.

(51) Int. Cl.
*B05D 5/12* (2006.01)
*H01C 17/00* (2006.01)

(52) U.S. Cl. ............ 427/79; 429/123; 429/126.3; 429/189; 429/190; 29/592.1; 29/610.1

(58) Field of Classification Search ........ 427/74, 427/79, 115, 123, 125, 126.3, 189, 190, 419.2; 429/30, 33, 304; 29/23.35, 592.1, 602.1, 29/610.1

See application file for complete search history.

(56) References Cited

U.S. PATENT DOCUMENTS

| 4,426,356 A | 1/1984 | Nair |
| 4,453,199 A | 6/1984 | Ritchic et al. |
| 4,484,943 A | 11/1984 | Miura et al. |
| 4,534,917 A | 8/1985 | Walz |
| 4,576,725 A | 3/1986 | Miura et al. |

(Continued)

FOREIGN PATENT DOCUMENTS

DE 4238688 5/1994

(Continued)

OTHER PUBLICATIONS

H. Gleiter, "Mechanical Properties and Deformation Behavior of Materials Having Ultra-Fine Microstructures," Nastasi et al. Ed., 3-35 1993, month is unknown.

(Continued)

*Primary Examiner*—Stephen J. Kalafut
(74) *Attorney, Agent, or Firm*—Foley & Lardner LLP

(57) ABSTRACT

Electronic devices prepared from nanoscale powders are described. Methods for utilizing nanoscale powders and related nanotechnology to prepare capacitors, inductors, resistors, thermistors, varistors, filters, arrays, interconnects, optical components, batteries, fuel cells, sensors and other products are discussed.

21 Claims, 10 Drawing Sheets

U.S. PATENT DOCUMENTS

| | | | |
|---|---|---|---|
| 4,588,575 A | 5/1986 | David | |
| 4,610,857 A | 9/1986 | Ogawa et al. | |
| 4,619,845 A | 10/1986 | Ayers et al. | |
| 4,642,207 A | 2/1987 | Uda et al. | |
| 4,721,610 A | 1/1988 | Yoshida et al. | |
| 4,842,832 A | 6/1989 | Inoue et al. | |
| 4,851,262 A | 7/1989 | McFeaters | |
| 5,128,081 A | 7/1992 | Siegel et al. | |
| 5,130,210 A | 7/1992 | Iwasaki et al. | |
| 5,147,448 A | 9/1992 | Roberts et al. | |
| 5,149,381 A | 9/1992 | Grewe et al. | |
| 5,149,596 A | 9/1992 | Smith et al. | |
| 5,258,338 A | 11/1993 | Maher | |
| 5,338,430 A | 8/1994 | Parsonage et al. | |
| 5,350,641 A | 9/1994 | Mogensen et al. | |
| 5,355,764 A | 10/1994 | Marinos et al. | |
| 5,368,951 A | 11/1994 | Shiratori et al. | |
| 5,403,375 A | 4/1995 | König et al. | |
| 5,407,458 A | 4/1995 | König et al. | |
| 5,414,588 A | 5/1995 | Barbee, Jr. et al. | |
| 5,417,956 A | 5/1995 | Moser | |
| 5,447,708 A | 9/1995 | Helble et al. | |
| 5,472,477 A | 12/1995 | König | |
| 5,483,735 A * | 1/1996 | Postma et al. | 29/603.16 |
| 5,486,277 A | 1/1996 | Barbee, Jr. et al. | |
| 5,486,435 A | 1/1996 | Brochu et al. | |
| 5,486,675 A | 1/1996 | Taylor et al. | |
| 5,503,081 A | 4/1996 | Lindblom et al. | |
| 5,507,965 A | 4/1996 | Padoy et al. | |
| 5,560,960 A | 10/1996 | Singh et al. | |
| 5,569,561 A | 10/1996 | Exnar et al. | |
| 5,590,387 A * | 12/1996 | Schmidt et al. | 419/36 |
| 5,624,718 A | 4/1997 | Dearnaey | |
| 5,665,277 A | 9/1997 | Johnson et al. | |
| 5,688,417 A | 11/1997 | Cadre et al. | |
| 5,709,786 A | 1/1998 | Friese et al. | |
| 5,770,022 A | 6/1998 | Chang et al. | |
| 5,788,738 A | 8/1998 | Pirzada et al. | |
| 5,851,507 A | 12/1998 | Pirzada et al. | |
| 5,874,134 A | 2/1999 | Rao et al. | |
| 5,876,683 A | 3/1999 | Glumac et al. | |
| 5,905,000 A | 5/1999 | Yadav et al. | |
| 5,935,461 A | 8/1999 | Witherspoon et al. | |
| 5,952,040 A * | 9/1999 | Yadav et al. | 427/126.3 |
| 6,042,900 A | 3/2000 | Rakhimov et al. | |
| 6,132,563 A | 10/2000 | Frach et al. | |
| 6,132,905 A | 10/2000 | Kumar et al. | |
| 6,468,497 B1 | 10/2002 | Khan et al. | |
| 6,600,127 B1 | 7/2003 | Peterson et al. | |
| 6,689,192 B1 | 2/2004 | Phillips et al. | |

FOREIGN PATENT DOCUMENTS

| | | |
|---|---|---|
| JP | 102110 | 4/1990 |
| SU | 1654258 | 6/1991 |

OTHER PUBLICATIONS

R. W. Siegel, "Mechanical Properties and Deformation Behavior of Materials Having Ultra-fine Microstructures," Nastasi et al. Ed., 509 1993, month is unknown.

Nieman et al., "J Mater. Res.," 6, 1012 1991, month is unknown.

Nieman et al., "Scripta Metall. et Mater.," 24, 145 1990, month is unknown.

Skandon et al., "Scripta Metall. et Mater.," 25, 2389 1991, month is unknown.

Eastman et al., "Mater. Res. Soc. Symp. Proc.," 155, 255 1989, month is unknown.

H. Hahn et al., "Mater. Res. Soc. Symp. Proc.," 196, 71 1990, month is unknown.

M. J. Mayo, Mechanical Properties and Deformation Behavior of Materials Having Ultra-fine Microstructures, 361 1993, month is unknown.

Beck and Siegel, "J. Mater. Res.," 7, 2840 1992, month is unknown.

Tamaki et al., "J. Electrochem. Soc.," 141, 2207 1994, month is unknown.

Sugaya et al., IEEE Trans. on Magnetics, 31, 2197 1995, month is unknown.

YeackScranton, "Nanomagentism," Kluwer Academic, Netherland, 1-6 1993, month is unknown.

Steigerwald and Brus, "Ann. Rev. Mater. Sci.,"19, 471 1989, month is unknown.

R. Uyeda, "Prog. Mater. Sci.," 35, 1 (1991), and R. W. Siegel, Materials Science and Technology, 15, VCH, Weinhem, 583 1991, month is unknown.

G. S. Springer, "Advances in Heat Transfer," 14, 281-341, Academic Press 1978, month is unknown.

S. Iwama et al, "Ultrafine Powders of TiN and AIN Produced by a Reactive Gas Evaporation Technique with Electron Beam Heating," Journal of Crystal Growth 56 (1982) 265-269, North-Holland Publishing Company, month is unknown.

Jacobson et al., Rapid Solidification Processing. Mat. Sci. and Eng., R11.335 1994, month is unknown.

R. Uyeda, "Studies of Ultrafine Particle in . . . ," Prog. Mater. Sci., 35, 1 1991, month is unknown.

R. W. Siegel, Materials Science and Technology. 15. VCH. Weinhem. 583 (1991), month is unknown.

H. Jones, "Splat Cooling and Metastable Phases," Rep. Prog. Phys. 36. 1425 1973, month is unknown.

Eastman et al., "Processing and Properties of Nanophase Oxides," Mater Res. Soc. Symp. Proc., 155, 255, 1989, month is unknown.

* cited by examiner

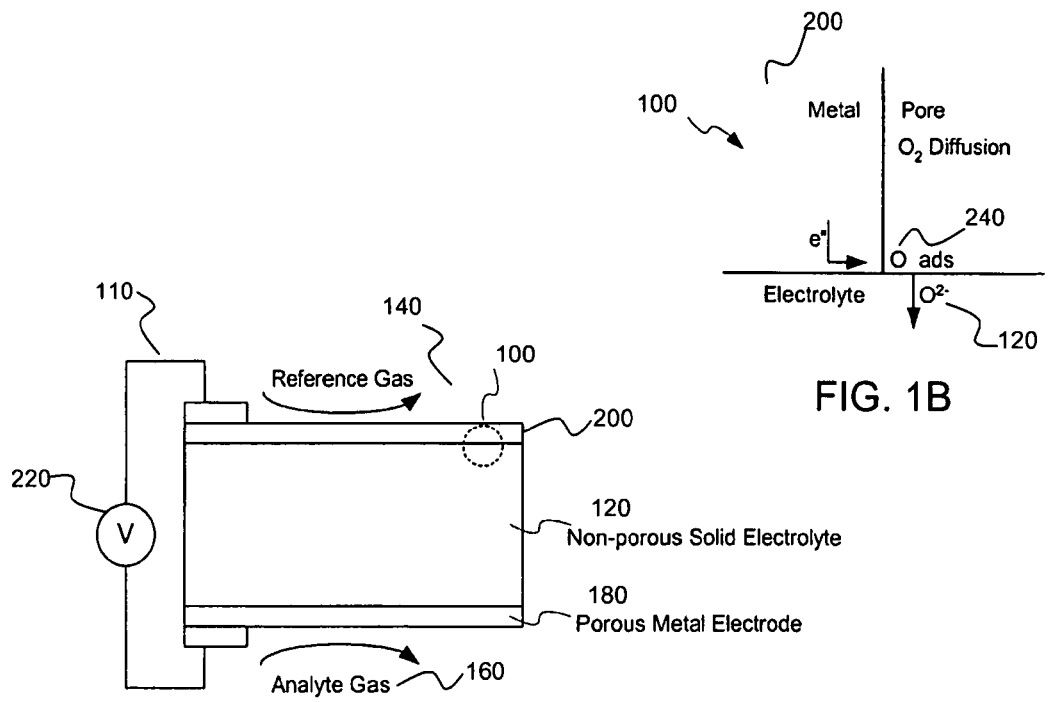
FIG. 1B
FIG. 1A
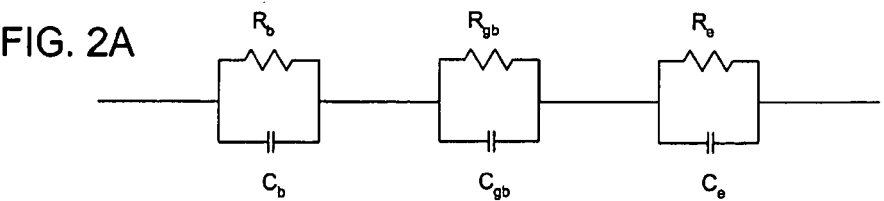
FIG. 2A
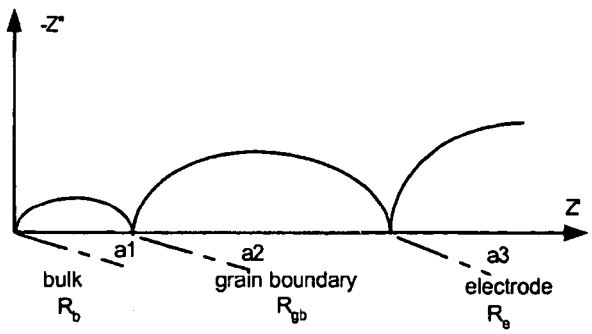
FIG. 2B

PRODUCTS COMPRISING NANO-PRECISION ENGINEERED ELECTRONIC COMPONENTS

This application is a continuation of U.S. Ser. No. 10/614,845 entitled "Nanostructured Powders and Related Nanotechnology," filed Jul. 08, 2003, now U.S. Pat. No. 7,081,267 which is a continuation of U.S. Ser. No. 09/988,901 entitled "Nanostructured Deposition and Devices", now issued as U.S. Pat. No. 6,610,355, filed Nov. 19, 2001, which is a continuation of U.S. Ser. No. 08/251,313 entitled "Nanostructured Solid Electrolytes and Devices," now issued as U.S. Pat. No. 6,387,560, filed on Feb. 17, 1999, which is a continuation of U.S. Ser. No. 08/739,257, entitled "Nanostructured Ion Conducting Solid Electrolytes", now issued as U.S. Pat. No. 5,905,000, filed Oct. 30, 1996, which is a continuation-in-part of U.S. Ser. No. 08/730,661, entitled "Passive Electronic Components from Nano-Precision Engineered Materials," now issued as U.S. Pat. No. 5,952,040, filed on Oct. 11, 1996, which is a continuation-in-part of U.S. Ser. No. 08/706,819,filed Sep. 3, 1996 entitled "Integrated Thermal Process and Apparatus for the Continuous Synthesis of Nanoscale Powders" now issued as U.S. Pat. No. 5,851,507 on Dec. 22, 1998, and U.S. Ser. No. 08/707,341, entitled "Boundary Layer Joule-Thompson Nozzle for Thermal Quenching of High Temperature Vapors," filed concurrently on Sep. 3, 1996, now issued as U.S. Pat. No. 5,788,738 on Aug. 4, 1998. These applications and patents are all commonly owned with the present application, and are all incorporated by reference herein.

BACKGROUND OF THE INVENTION

1. Field of the Invention

This invention pertains in general to ion conductors and to processes for the synthesis of ion conducting solid electrolytes. In particular, the invention relates to the use of nanoscale powders for the preparation of nanostructured oxygen ion conducting electrolytes.

2. Description of the Prior Art

Solid electrolytes are materials through which ion species can migrate with low energy barriers. Table 1 outlines some examples of ion-conducting structures, representative materials, and the ions conducted. These materials are of critical commercial importance to electrochemical devices, components and processes. Illustrative applications include sensors, batteries, fuel cells, ion pumps, membrane reactors, catalysis, and metallurgy.

| REPRESENTATIVE MATERIALS | ION CONDUCTED |
| --- | --- |
| Stabilized $ZrO_2$ System, Stabilized $Bi_2O_3$ System, Ceria, Perovskites | $O^{2-}$ |
| Beta-Alumina, NASICON Systems | $Na^+$ |
| AgI, $RbAg_4I_5$ | $Ag^+$ |
| $Rb_4Cu_{16}I_7Cl_{13}$ | $Cu^+$ |
| $Li_3N$, $Li_2S$—$SiS_2$—$Li_3PO_4$ System, Organic Polymer Systems, LISICON Systems | $Li^+$ |

As a specific example, stabilized zirconia is a known conductor of oxygen ions. Accordingly, its properties are utilized in various fields of technology, such as in oxygen sensors for fuel-air ratio optimization of automobiles and furnaces, in oxygen pumps for solid state oxygen separation, in solid-oxide fuel cells for noiseless and clean power generation from chemical energy, and in catalytic membrane reactors.

The oxygen-ion conduction properties of stabilized zirconia used in a typical oxygen sensor are well understood based on electrochemical-cell theory. When placed between two compartments containing a reference gas and an analyte oxygen gas at different partial pressures, stabilized zirconia functions both as a partition between the two compartments and as an electrochemical-cell electrolyte. Under ideal conditions, the open-circuit EMF ($E_0$) of the cell is given by the known Nernst equation:

$$E_0 = \frac{RT}{4F} \ln\left(\frac{PO_{2REF}}{PO_2}\right), \quad (1)$$

where T is the absolute temperature of the cell; $PO_2^{Ref}$, and $PO_2$ are the partial pressures of oxygen in the reference and analyte compartments, respectively; R is the universal gas constant; and F is Faraday's number.

According to this equation, any difference in partial pressure of the oxygen across the two faces of the oxygen-conducting electrolyte generates an electromotive force that depends on the temperature and partial-pressure ratio of the oxygen in the two compartments of the system. In order to generate Nernstian response in sufficiently short times, the temperature of stabilized $ZrO_2$ needs to be high (above 700° C.), which results in relatively high power requirements and in increased equipment mass and size, need for insulation, and attendant sealing problems. These considerations often produce unsatisfactory performance or affect the commercial viability of products based on stabilized $ZrO_2$ technology.

The inherent reasons for the high-temperature requirement and the corresponding performance problems of present-day oxygen ion conducting electrolyte based devices can be traced to the reaction mechanism of the cell and the microstructure of the sites where the reaction occurs. Referring to FIG. 1A, a schematic drawing of a $ZrO_2$ sensor cell 110 is illustrated, where the stabilized zirconia is modeled as a solid electrolyte membrane 120 between a first compartment 140 containing a reference oxygen atmosphere at a predetermined partial pressure $pO_2^{Ref}$, and another compartment 160 containing an analyte gas oxygen at a different partial pressure $PO_2$. The two sides of the stabilized zirconia non-porous solid electrolyte 120 are coupled through an external circuit connecting an anode 180 and a cathode 200 made of porous metal, such as silver. The anode 180 is the cell electrode at which chemical oxidation occurs and the electrons released by the oxidation reaction flow from it through the external circuit to the cathode. The cathode 200 is the cell electrode at which chemical reduction occurs. The cell electrolyte 120 completes the electrical circuit of the system by allowing a flow of negative ions $O^{2-}$ between the two electrodes. A voltmeter 220 is provided to measure the EMF created by the redox reactions occurring at the interfaces of the electrolyte with the two oxygen atmospheres.

Thus, the key redox reaction of the cell occurs at the points where the metal electrode 200, the electrolyte 120 and the gas meet (illustrated in FIG. 1B the insert 100 of FIG. 1A as the "triple point" 240). At each such site on the surface of the electrolyte 120, the redox reaction is as follows:

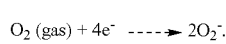 (2)

$$O_2 \text{ (gas)} + 4e^- \longrightarrow 2O_2^-.$$

Since the reaction and the electrochemical performance of the sensor depend on the redox kinetics, the cell's performance is a strong function of the concentration of triple points. In other words, an electrode/electrolyte/electrode cell with as many triple points as possible is highly desirable [see Madou, Marc and M. Morrison, *Chemical Sensing with Solid State Devices*, Academic Press, Boston (1989)]. In the case of an oxygen cell with a $ZrO_2$ solid membrane and silver electrodes, this requirement corresponds to maximizing the triple points on each side of the $PO^2.Ag'/ZrO_2/Ag''PO_2^{Ref}$ system.

Another cause of poor performance of oxygen-sensor cells can be explained with the help of complex-impedance analysis. Referring to FIGS. 2a and 2b, a complex impedance diagram for a $ZrO_2$ sensor is shown, where the impedances of the bulk, grain boundary and electrode are illustrated in series to reflect their contribution to the ionic conduction at each triple point. It has been shown that the conductive performance of electrolytes at temperatures below 500° C. is controlled by the grain boundary contribution to the overall impedance. Thus, for significant improvements of the conductivity at low temperatures, it is necessary to significantly minimize the grain-boundary (interface) resistance.

In summary, oxygen ion conducting devices based on stabilized-zirconia electrolyte have two problems that can be traced to material limitations. First, the electrolytes have high impedance; second, the concentration of triple points is relatively low. These problems are common to solid oxygen-conducting electrolytes in particular and solid electrolytes in general, and any improvement in these material characteristics would constitute a significant technological step forward. The present invention provides a novel approach that greatly improves these aspects of ion conducting solid electrolytes.

SUMMARY OF THE INVENTION

One of the objectives of this invention is to enhance the ion-conductivity of solid electrolytes by preparing nanostructured solid electrolytes.

Another objective is to reduce the electrolyte thickness with the use of nanostructured precursors of solid electrolytes.

A further objective is to enhance the concentration of triple points in the ion conducting devices by using nanostructured precursors and materials.

Yet another objective of the invention is to utilize the unique properties of size confinement in solid electrolyte and electrode grains when the domain is confined to less than 100 nanometers.

Another objective of this invention is an oxygen-conducting electrolyte material with low-impedance oxygen conducting characteristics.

Another objective of the invention is an oxygen ion conducting device with a very high density of triple points.

Another goal is a process and materials that reduce the cost of manufacture of products that incorporate oxygen-ion conductors.

Yet another goal is a process and materials that reduce the cost of operation of products that incorporate oxygen-ion conductors.

Finally, another goal is a process that can be readily incorporated with conventional methods for manufacturing products containing ion-conducting electrolytes.

Various other purposes and advantages of the invention will become clear from its description in the specification that follows and from the novel features particularly pointed out in the appended claims. Therefore, to the accomplishment of the objectives described above, this invention comprises the features hereinafter illustrated in the drawings, fully described in the detailed description of the preferred embodiments and particularly pointed out in the claims. However, such drawings and description disclose only some of the various ways in which the invention may be practiced.

BRIEF DESCRIPTION OF THE DRAWINGS

FIGS. 1A and B are schematic drawings of a $ZrO_2$ solid electrochemical cell where the stabilized zirconia is modeled as a solid electrolyte membrane sandwiched between a first compartment containing a reference oxygen atmosphere at a predetermined partial pressure and another compartment containing an analyte gas with oxygen at a different partial pressure.

FIGS. 2a and 2b are a complex impedance diagram for a $ZrO_2$ sensor, where the impedances of the bulk, grain boundary and electrode are illustrated to reflect their contribution to the ionic conduction at each triple point shown in FIG. 1B.

DETAILED DESCRIPTION OF THE INVENTION

This invention is based on the recognition that the ion conductivity of polycrystalline solid electrolytes at moderate and near-ambient temperatures is mainly controlled by the conductivity of grain boundary and the concentration of triple points. The invention further notes that the engineering of grain boundary resistance and triple points in solid electrolyte devices is limited by the electrolyte thickness and electrode characteristics, respectively, which in turn depend on grain size of the precursors and the material used in the manufacture of electrolytes and electrodes for solid ion conductors in general, and solid oxide oxygen sensors, solid oxide oxygen pumps and solid oxide fuel cells in particular. These limitations constitute an inherent obstacle to achieve significant technological improvements.

The finest powders currently available for commercial use consist of particles with sizes in the order of several microns. For example, the YSZ powders that are presently used to produce oxygen sensors have an average grain size of about 1 to 3 microns. Since the number of triple points occurring within a given area at the interface with the oxygen atmosphere is necessarily limited by the number of electrode grains distributed within that area, the grain size in the electrode is very important for maximizing redox-reaction sites. Similarly, since we know that the impedance of the system is reduced by electrolyte thickness, it follows that thinner electrolytes produced from smaller grains would produce lower impedance. Accordingly, the heart of this invention consists of using nanosize materials in the manufacture of electrolytes for these applications.

The current inability to improve the performance of solid ion conductors is a result of the inability of prior-art processes to economically reduce powder size of precursor materials beyond the micron-size range. Accordingly, the present invention is based on the work disclosed in commonly-owned U.S. Pat. Nos. 5,851,507 and 5,788,738 which provide a viable vehicle for manufacturing, nanoscale powders suitable for the present invention. Material having with physical properties as produced by the process and apparatus described therein is a necessary ingredient for practicing this invention on a commercial scale.

Manufacturing Nanoscale Powders

Figure 13:
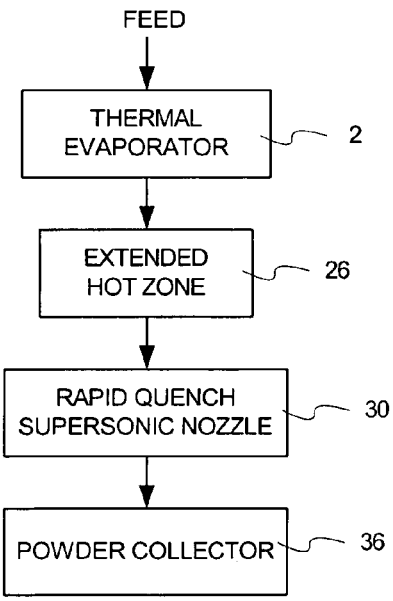
FIG. 13 is a block diagram of the thermal process of the present invention for the continuous synthesis of nanoscale powders.
Figure 14:
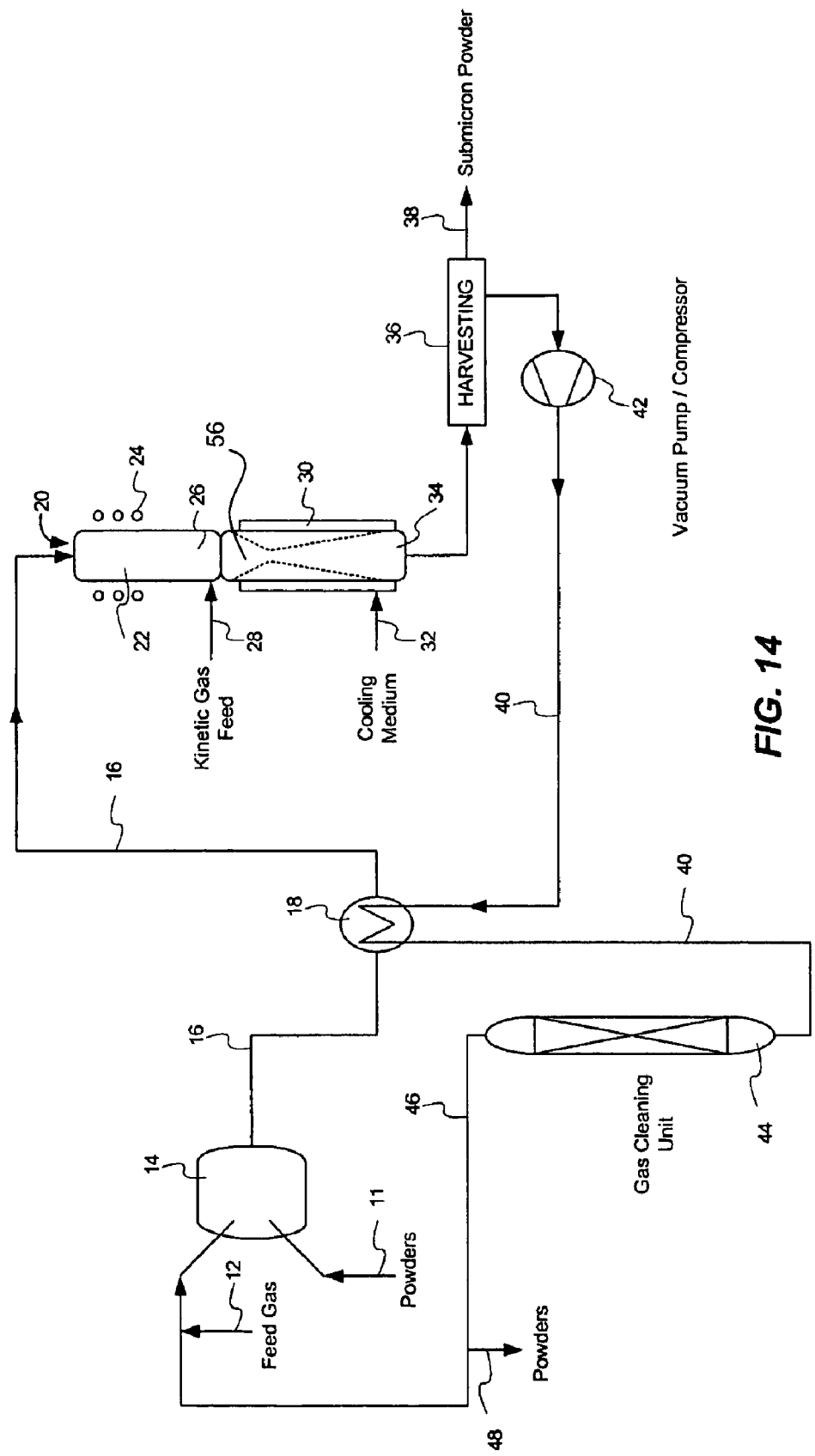
FIG. 14 is a schematic representation of the process for the continuous synthesis of nanoscale powders, including the adiabatic-expansion, thermal-quenching step of the invention.

As set out in U.S. Pat. No. 5,788,738, which is incorporated by reference herein, FIGS. 13 and 14 show a block diagram and a schematic flow diagram, respectively, of a thermal process for the continuous synthesis of nanoscale powders as applied to solid precursors such as metals, alloys, ceramics, composites, and combinations thereof with particle size (normally greater than 1 micrometer) suitable for continuous vaporization in a gas stream.

A feed stream 11 of a precursor material in powder form is premixed with a feed gas stream 12 (such as argon, helium, nitrogen, oxygen, hydrogen, water vapor, methane, air, or a combination thereof, depending on the particular precursor being processed and the corresponding atmosphere—inert, oxidizing, or reducing—required for the process) in mixing apparatus 14 appropriate to create a suspension. The powder 11 is suspended in the gas 12, preferably in a continuous operation, using fluidized beds, spouting beds, hoppers, or combinations thereof, as best suited to the nature of the precursor. The resulting gas-stream suspension 16 is advantageously preheated in a heat exchanger 18 and then is fed into a thermal reactor 20 where the suspended powder particles are partially or, preferably, completely evaporated in a thermal evaporation zone 22 by the input of thermal energy. The source 24 of such thermal energy may be internal energy, heat of reaction, conductive, convective, radiative, inductive, microwave, electromagnetic, direct or pulsed electric arc, nuclear, or combinations thereof, so long as sufficient to cause the rapid vaporization of the powder suspension being processed. Optionally, in order to prevent contamination of the vapor stream caused by partial sublimation or vaporization of the thermal reactor's interior walls, they may be pre-coated with the same material being processed.

The vaporized gas-stream suspension next enters an extended reaction zone 26 of the thermal reactor that provides additional residence time, as needed to complete the evaporation of the feed material and to provide additional reaction time (if necessary). As the stream leaves the reactor, it passes through a zone 56 where the thermokinetic conditions favor the nucleation of solid powders from the vaporized precursor. These conditions are determined by calculating the supersaturation ratio and critical cluster size required to initiate nucleation. Rapid quenching leads to high supersaturation which gives rise to homogeneous nucleation.

Using titanium powder as an example, based on the physical properties of the feed material and operating conditions in the reactor (size=10 microns, melting point=1,660° C., boiling point=3,287° C., heat of vaporization of titanium=10.985 Btu/g, hot gas temperature=4,000° C.), it is possible to calculate the residence time required for vaporization (2.32 msec for heating to melting point, 0.265 msec for melting, 5.24 msec for vaporization; total time required=8-10 msec). Based on the velocity of the suspension injected into the reactor and the travel distance through the reactor, one can determine that a velocity of about 46 ft/sec produces a residence time of 10.7 msec, sufficient for vaporization. If the process requires a predetermined thermokinetic state of the powder being processed which can be enhanced by the presence of a particular gas, a kinetic gas feed 28 (such as argon, helium, nitrogen, oxygen, hydrogen, water vapor, methane, air, or combinations thereof) can also be mixed with the precursor vapor to reach the desired thermokinetic state. As soon as the vapor has begun nucleation, the process stream is quenched in a converging-diverging nozzle-driven adiabatic expansion chamber 30 at rates at least exceeding 1000 K/sec, preferably greater than 1000000 K/sec, or as high as possible. As further detailed below, a cooling medium 32 is utilized for the converging-diverging nozzle to prevent contamination of the product and damage to the expansion chamber 30. Rapid quenching ensures that the powder produced is homogeneous, its size is uniform and the mean powder size remains in submicron scale.

The quenched gas stream 34 is filtered in appropriate separation equipment 36 to remove the submicron powder product 38 from the gas stream. As well understood in the art, the filtration can be accomplished by single stage or multistage impingement filters, electrostatic filters, screen filters, fabric filters, cyclones, scrubbers, magnetic filters, or combinations thereof. The filtered nanopowder product 38 is then harvested from the filter 36 either in batch mode or continuously using screw conveyors or gas-phase solid transport and the product stream is conveyed to powder processing or packaging unit operations (not shown in the drawings). The filtered gas stream 40 is compressed in a vacuum-pump/compressor unit 42 and cooled by preheating the gas-stream suspension 16 in heat exchanger 18. Thus, the enthalpy of compression can be utilized by the process as process heat through heat integration. Stream 40 is then treated in a gas cleaning unit 44 to remove impurities and any undesirable process product gases (such as CO, $CO_2$, $H_2O$, HCl, $NH_3$, etc). The gas treatment can be accomplished by single stage or multistage gas-gas separation unit operations such as absorption, adsorption, extraction, condensation, membrane separation, fractional diffusion, reactive separation, fractional separation, and combinations thereof. Finally, the treated gases 46 are recycled back to be reused with the feed gas stream 12. A small split stream 48 of the compressed treated gas 46 is purged to ensure steady state operation of the continuous thermal process.

Figure 3:
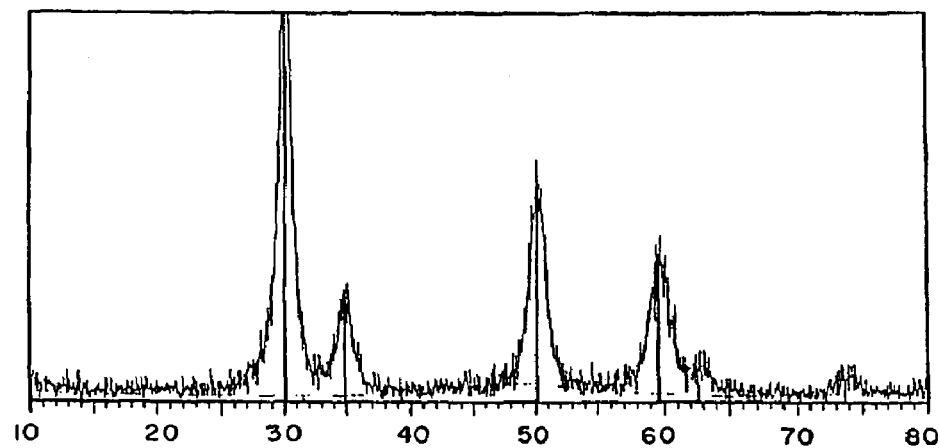
FIG. 3 is an X-ray diffraction pattern of the nanoscale yttria stabilized zirconia precursor used to form an electrolyte membrane according to the invention.
Figure 15:
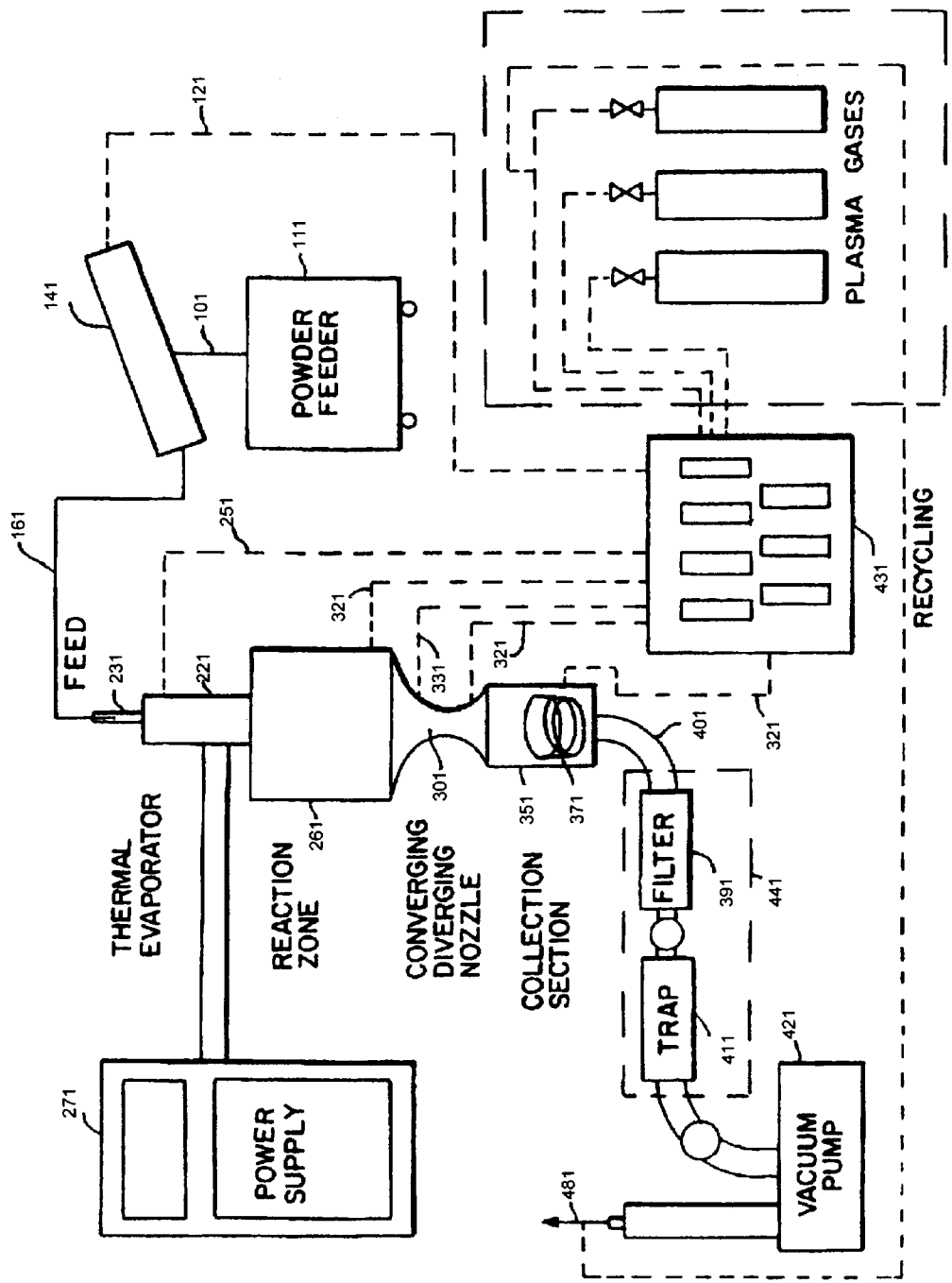
FIG. 15 is a schematic illustration of a pilot-plant process according to the preferred embodiment of the invention.

The invention was reduced to practice in a pilot plant illustrated schematically in FIG. 3 15. This thermal reactor system consists of an upper, cylindrical, thermal evaporation chamber 221 made of quartz and cooled by circulating water (not shown). The gas-stream suspension 161 is formed by mixing the solid feed material 101 fed by a powder feeder 111 with an inert gas stream 121 such as argon. The suspension 161 is injected continuously from the top of the thermal evaporation chamber 221 through a water-cooled injection probe 231 and is heated inductively by means of an RF plasma torch 241 (consisting of a plasma-gas source 251 and a suitable power supply 271 ). The reactor also comprises another, cylindrical, extended reaction zone 261 made of water-cooled stainless steel, positioned downstream of the thermal evaporation zone 221 and sufficiently large to provide the vaporized stream with the residence time required to complete the vaporization and reaction. The reaction zone 261 is lined with a zirconia refractory felt and a layer of silicon-carbide refractory material to reduce heat losses from the hot reaction zone. If necessary to prevent contamination of the reacting fluid by the reactor or refractory material, the reactor's interior walls (and refractory lining) may be further lined with the same material constituting the solid feed.

Figure 4:
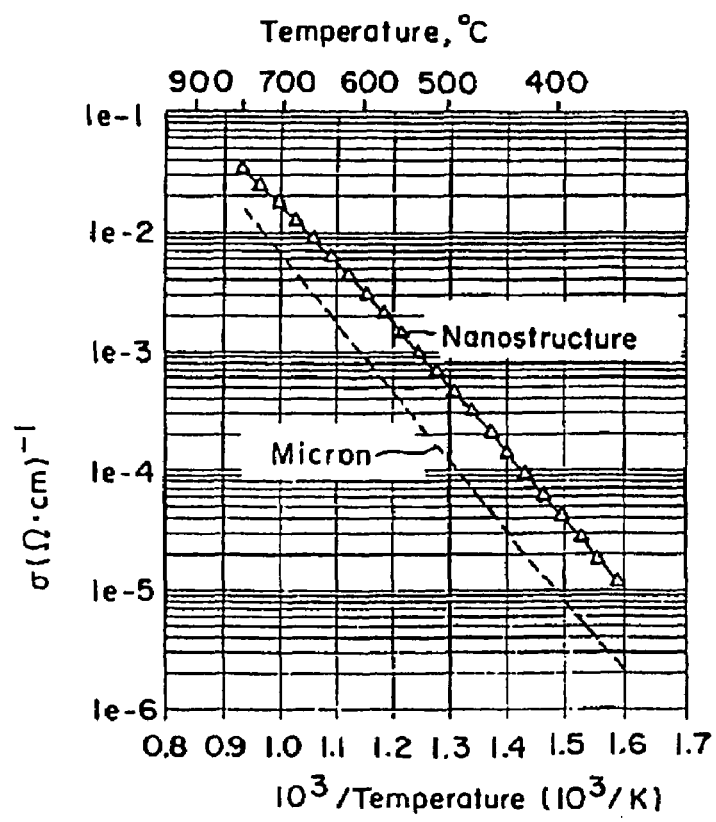
FIG. 4 is a graph of total conductivity versus temperature of 9-YFSZ nanozirconia prepared by the process of Example 1 and micron-based YFSZ material.

The adiabatic expansion chamber 301 consists of a Joule-Thompson converging-diverging nozzle (also known as a deLaval nozzle) having uniformly converging and diverging sections, as also illustrated in detail in FIG. 4 of U.S. Pat. No. 5,788,735. The nozzle is operated with a pressure drop (created by the vacuum pump 42421 operated at least 50 Torr, normally between 100 and 650 Torr) sufficient for quenching the high-temperature vapors produced upstream in the reactor by plasma induction. The separation system 361 of the invention is realized by means of a collection chamber 351 attached to the outlet of the expansion chamber 301, where the very find particles entrained in the gaseous stream are collected on a water-cooled metallic coil 371 (copper was used successfully for the test runs detailed below) and periodically extracted. It is anticipated that commercial-scale equipment would incorporate a screw or similar conveyor for the continuous removal of the nanopowder product from the collection chamber 351. The gas stream 401 out of the collection chamber is further passed through a filter 391 and trap 341 to thoroughly clean it prior to passage through the vacuum pump 421. A monitor and fluid-control panel 431 is utilized to monitor process variables (temperatures, pressures, water and gas flow rates), record them, and control all water and gas streams to maintain steady-state operation. It is noted that for simplicity the gas stream 481 exhausted from the vacuum pump 421 was not recycled in the demonstration plant of FIG. 15 but a commercial application would preferably do so for energy and material conservation.

In a continuous, steady-state process, the quench rate can be changed by changing the rate of expansion, which provides a much-sought form of control over the nucleation process of nanopowders produced by vapor condensation. Since it is known that the size, size distribution and other properties of vapor condensation products depend on the speed at which the nucleating material is quenched, the adiabatic expansion approach of the present invention provides an invaluable tool, missing in all prior-art processes, for controlling the quality of the resulting nanopowders. In addition, because the process can be carried out stably in continuous fashion, it provides a suitable vehicle for large scale applications and commercial production of bulk nanomaterials.

Figure 16:
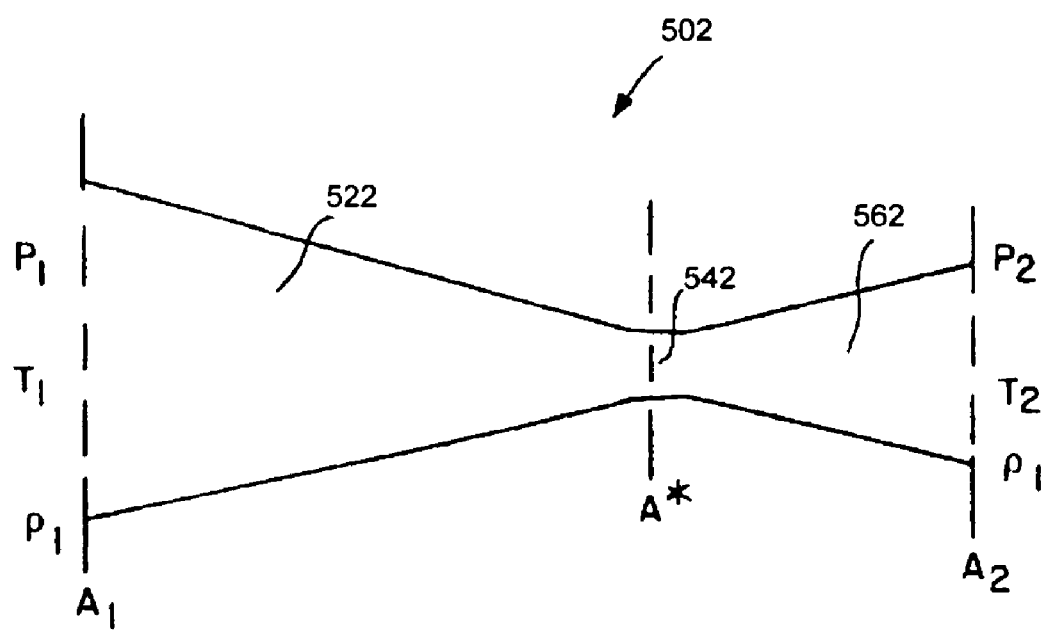
FIG. 16 is a sketch of a converging diverging nozzle to illustrate the relationship between parameters of the process carried out with the nozzle of the invention.

FIG. 16 is a sketch of a converging-diverging nozzle 502 to illustrate the relationship between critical parameters of the process and of the nozzle used to carry out the invention. It consists of an optimally-shaped combination of a convergent section 522 a throat section 542 and a divergent section 562. At steady state, the condensing fluid is restricted through a uniformly decreasing cross-section $A_1$ from an initial cross-section $A_1$ at pressure $P_1$ and temperature $T_1$, it is passed through the cross-section $A^*$ of the throat 542 and then it is expanded through a final cross-section $A_2$ at pressure $P_2$ and temperature $T_2$. The process is carried out through a cross-section A that is first uniformly decreasing and then uniformly increasing through the device. In the converging section 522 the Mach number M for the nozzle is less than 1, while it is equal to 1 in the throat 542 and greater than 1 in the diverging section 562. (Mach number is defined as the ratio of the hydrodynamic flow velocity to the local speed of sound.) Therefore, the initial subsonic flow is accelerated in the converging section of the nozzle, and the flow expands supersonically in the divergent section of the nozzle. At any cross-section A, the Mach number is given by the local value of $A/A^*$, with m=1 at the throat.

Preparing Electronic Components

As set out in U.S. patent application Ser. No. 08/730,661, now U.S. Pat. No. 5,952,040, which is incorporated by reference herein and reproduced in part here for convenience, the present invention is based on the utilization, as precursor material, of powders having a particle size smaller than the critical length characteristic of the property of interest for the material and on the preparation of nanostructured films for the fabrication of passive electronic components. The work disclosed in commonly owned applications Ser. No. 08/706,819 (now U.S. Pat. No. 5,851,507) and Ser. No. 08/707,341 (now U.S. Pat. No. 5,788,738) provides a viable vehicle for manufacturing nanoscale ceramic powders suitable for the present invention.

As defined in the art, submicron powders are materials having average grain size below 1 micrometer. Of critical interest for this invention are nanoscale powders and nanostructured layers of ceramics and electrodes. Nanoscale powders (nanopowders) are submicron powders with average grain size less than 100 nanometers (preferably with a standard deviation of less than 25 nm) and with a significant fraction of interfacial atoms. Accordingly, reference to nanoscale powders in this disclosure is intended to refer to powders with those characteristics, but it is understood that the critical length for a given property of a material may be smaller or larger, depending on the property of interest, although such length is always submicron.

Submicron layers are layers having thickness less than 1 micrometer. Of particular interest to this invention are nanostructured layers which are defined specifically as layers with thickness, or microstructure, or both, confined to a size less than property confinement size (positively less than 1 micron, preferably below 100 nm). Accordingly, reference to nanostructured layers in this disclosure is intended to refer to layers with those characteristics.

As discussed in the copending applications, it is known that within these size ranges a variety of confinement effects occur that dramatically change the properties of the material. A property will be altered when the entity or mechanism responsible for that property is confined within a space smaller than some critical length associated with that entity or mechanism. For example, a normally ductile metal will become significantly harder if its grain size is reduced to the point where moving dislocations through its crystal lattice are no longer able to occur at normal levels of applied stress. Since the stress required to produce a Frank-Read dislocation is inversely proportional to the spacing between its pinning points, as one skilled in the art would readily understand, a critical length in this case is that for which the stress necessary to produce a dislocation becomes larger than the conventional yield stress for the given material.

Thus, confinement effects can be exploited to produce extremely hard and strong materials with much higher yield stress than exhibited by the conventional form of their precursors. Nanostructured devices prepared from nanopowders feature grain sizes too small for Frank-Read dislocation to operate in the conventional yield stress domain and, consequently, enhancement in strengths and hardness of 100% to 500% are observed in films and pellets made from nanopowders (important to all passive components). Similarly, nanostructured layer devices with a grain size confined to a dimension less than the mean free path of electrons are expected to exhibit resistivities that are higher by orders of magnitude greater than conventional materials (important for resistors and EMI filters). If the nanostructured grains are confined to a dimension smaller than the domain size of magnetic materials, the resulting devices are expected to exhibit dramatically higher permeability (important to inductors and EMI filters), novel properties such as giant magneto-resistance (GMR), and superparamagnetic effects. Nanostructured grains are nanoscale and therefore enable the manufacture of ultrathin nanostructured layers of ceramic and electrode (important to capacitors, varistors, resistors, inductors and EMI filters) and greater miniaturization of all these devices.

Nanostructured materials also offer the opportunity for near-molecular blending of dopants and property modifiers. This is very important because commercial passive components are not prepared from a single component; instead, the ceramic layer is made of a formulation that consists of several components (from five to seventeen are reported in the literature), each added to provide the desired matrix of performance characteristics over the device's lifetime and usage environment. Near-molecular blending can enhance device reliability and reproducible performance, particularly when the device footprint keeps getting smaller. Nanoscale composites of electrodes can reduce the need for expensive alloys and yet ensure the desired electrical performance at miniaturized scale. Nanostructured electrodes also offer very high surface area and modified electrochemical properties, which are important for boundary layer and electrolytic passive components.

From a processing viewpoint, nanopowders offer very high surface area, which leads to enhanced interfacial diffusivities; enhanced diffusivities in turn enable rapid, low temperature consolidation, sintering, and forming of normally difficult-to-process materials. This effect is very important because it lowers the temperatures required for sintering and densifying the powder precursors laid to form ceramic layers. Densification by sintering is a necessary step to eliminate openings between grains of ceramic material that might cause failure of the ceramic layer and therefore of the passive electronic component. While sintering of dielectric materials prepared by prior-art processes requires temperatures in excess of 1,050° C., densification of the nanopowder layers formed by the process of the invention can be carried out at temperatures as low as 850° C.

The grain size of nanostructured materials is less than the wavelength of visible light; consequently, unique optical materials with grain sizes tailored for excitonic interactions with particular wavelengths can be prepared. Nanopowders are isomorphic because of dimensional confinement. Furthermore, enhanced solubilities are observed leading to non-equilibrium compositions. These characteristics offer the potential for catalysts with extremely high surface areas, high selectivity and activity. Finally, nanopowders feature quantum confinement to dimensions less than Debye length, which leads to electrochemical properties with order-of-magnitude higher sensitivities to chemical species.

Nanopowders, in summary, can enable the manufacture of nanostructured layers of ceramics, or alloys, or metals, or composites, or combinations thereof, and can lead to greater miniaturization of many devices. This approach can lead to devices with commercially desirable and unique properties (capacitor arrays, resistor arrays, inductor arrays, varistor arrays, EMI filters, thermistors, piezo-devices, magnetic devices, optics, electronic, magneto-optical, interconnects, membranes, biomedical, photoelectric, thermoelectric devices, ion-conducting electrolytes, batteries, fuel cells, and sensors).

In reference to capacitors, the invention becomes more clear when capacitor fundamentals are considered. The volume efficiency of a capacitor is given by the equation $$C/v = (\epsilon_0 K)/L^2 \quad (3)$$

where $\epsilon_0$ (=8.85 pF/m) is the permittivity of vacuum, K is the dielectric coefficient, and L is the thickness of the dielectric layer. This expression suggests that the capacitance and volumetric efficiency of ceramic capacitors can be increased if the dielectric layer thickness can be reduced. Thus, reductions in dielectric thickness can lead to ultrathin capacitors with higher volumetric efficiency.

The energy density of a capacitor, E/m, it is given by the equation:

$$E/m = 0.5(CV^2/m) = (\epsilon_0 K V^2)/(2\rho L^2) \quad (4)$$

where $\rho$ is the density of the dielectric material, and V is the applied voltage. Again, the relevance of ultra-thin ceramic layer is apparent from the above equation, which suggests that a significant reduction in dielectric thickness can dramatically increase the energy density of the capacitor. Given the fact that nanopowders have powder size that is less than an order of magnitude smaller than conventional precursor powders, the invention offers the potential for improving the performance envelop of capacitors by several orders of magnitude. The unique properties of band-gap engineering and size confinement effects further enhance the service that this invention can provide.

In reference to varistors, the voltage $V_{1\,mA}$ corresponding to 1 mA current through the varistor is commonly defined as the reference breakdown limit voltage. Varistors are rated for continuous operation at approximately $0.8 \times V_{1\,mA}$. Experimental investigations have established that $V_{1\,mA}$ for varistors can be expressed by:

$$V_{1\,mA} = nL/d_g \qquad (5)$$

where n is the nominal voltage drop per interface, L is the thickness of the ceramic layer in the varistor, and $d_g$ is the average size of the grains. It is noted that $V_{1\,mA}$ is independent of the chemical composition and fabrication process of the varistor. Thus, practical ways of increasing the voltage breakdown voltage are: (a) increasing the varistor thickness, and (b) decreasing the grain size. Of these alternatives, present-day processing technology only allows variation in "L," the varistor thickness, while grain size variations are an appealing but commercially unrealizable option. Nanopowders offer the opportunity to reduce the grain size by more than an order of magnitude and therefore can enhance the $V_{1\,mA}$ for a given thickness, or can help miniaturize the varistor, by more than 10 fold for the same voltage surge protection. The invention offers the potential of integrating nanostructured voltage surge layers with active electronic layers and chip. As for capacitors, the size confinement effects further enhance the scope of service that this invention can provide.

With reference to resistors, as would be apparent to those skilled in the art, the resistivity of a material is a function of the mean free path of electrons in the material. More specifically, the resistivity can be derived from the following equation:

$$r = m v_E / (n q^2 \lambda) \qquad (6)$$

where r is the resistivity, m is the electron mass, $v_E$ is Fermi's energy, n is the number of free electrons per unit volume in the material, q is the electron charge, and $\lambda$ is the electron mean free path. Thus, the resistivity of a material is inversely proportional to the mean free path of electrons in the material. In conventional material formulation used for preparing resistors, the domain size of the material formulation is greater than the mean free path of electrons and therefore resistivity changes can only be accomplished by changes in composition, phase, dopants, temperatures, fields, and voltage. However, if the material=s domain size is confined to a size less than the mean free path, as would happen in the case of nanostructured layers, the basic assumption that led to this equation is no longer valid. Therefore, the use of nanosize powders and nanostructured layers with domain size less than the mean free path of electrons is a significant and unique opportunity for preparing unique and commercially useful resistors.

Finally, with reference to inductors, the energy density, E/v, of a ceramic inductor is given by:

$$E/v = \frac{1}{2}(L/v)I^2 \qquad (7)$$

where I is the current through the inductive circuit. Combining this with the volumetric efficiency of a ceramic inductor, L/v, which can be given by:

$$L/v = \mu_i (4\pi N^2)/C_o \qquad (8)$$

where $\mu_i$ is the initial permeability, N is the number of turns, and $C_o$ is the core constant, produces the following equation:

$$E/v = \frac{1}{2}[\mu_i(4\pi N^2)/C_o]I^2 \qquad (9)$$

This expression suggests that the energy density of ceramic inductors can be increased by: (a) increasing the initial permeability of the ceramic; (b) decreasing the core constant; and (c) increasing the current carrying capability of the coil. From a design point of view, the impact of the initial permeability is the most accessible parameter. For example, the energy density of the inductor can be increased by two to four orders of magnitude if the permeability of existing soft magnetic materials can be increased by two to four orders of magnitude. Conventional materials are based on bulk, macroscopic, non-confined properties and the bulk properties values cannot be appreciably engineered. Thus, for inductors—like capacitors, resistors, and varistors—this invention offers materials with properties and performance modified because of domain confinement effects to nanoscale regime. Given the fact that confinement effects can increase resistivities and initial permeabilities, nanostructured layers indeed offer a significant service to inductor users.

Thus, as apparent from the examples of this disclosure, the fundamental breakthrough of the present invention is the preparation of nanostructured layers of ceramics and electrodes and the application of nano-precision engineered powders to passive electronic component manufacturing. According to the preferred embodiment of the invention, a conducting metal is deposited as an electrode layer on a substrate for mechanical support. The electrode composition can be any metal or alloy, or a composite containing any metal or alloy, with a melting point higher than 900° C., the following being the most preferred: Pt, Pd, Au, Ag, Cu, Ni or alloys thereof. The electrode layer thickness can vary from a few Angstroms to as thick as desired for the particular application and can be deposited by tape casting, screen printing, chemical precipitation, electrochemical techniques, photochemical techniques, sputtering, CVD, PVD, powder metallurgy, or combinations thereof.

Once the electrode has been formed, a film of any desired ceramic material formulation is formed on the electroded surface by one of three ways. According to one method, a well mixed suspension of ceramic nanopowders is prepared and the electroded surface is coated with a ceramic layer from the prepared nanopowder suspension, the resulting film is dried, and the deposition and drying steps are repeated as many times as desired. The suspension medium can be inorganic or organic, but preferably has low viscosity, high density, low vapor pressure, is chemically inert, environmentally benign, and inexpensive. The powders are preferably as small as possible (less than 100 nm), as monodisperse as possible (preferably with standard deviation less than 25 nm), clean at the surface, with minimal surface charge or agglomeration, and spherical. The ceramic nanopowder suspension can be supplemented for property enhancements with additives and for processing ease with binders and aids such as polyethylene glycol and organometallic coupling agents. The deposition process can be manual or automatic, forced or gravity assisted, vertical or inclined, linear or rotating (e.g. spin coating), and with substrate stationary and suspension flowing (e.g. printing, casting) or substrate moving and suspension stationary (e.g. dipping), or a combination of these. The drying step can be accomplished by conductive, or convective, or radiative heating, or combination of these, and can be assisted by controlling the composition of the gas environment. It is preferred that the gas environment during heating be such that it does not adversely react or reduce or oxidize the ceramic or electrode layers.

According to a second method, the nanopowders are deposited on the electroded surface by a vapor deposition process. The nanopowders are suspended in flowing gas and impact deposited on the electroded surface. The gas suspension may be heated or charged or accelerated to assist the deposition process. Once the nanopowder has been deposited, it may be pressed. This method does not require the drying step.

A third method is similar to the first one outlined above, the difference being primarily in the fact that in this method a solution of nanostructured precursors is prepared and then the nanopowders are precipitated directly onto the electrode surface. After the nanopowders have been deposited from the solution, the same steps of the first method are followed.

Multilayer components can be formed in two different ways. In a first method, the steps of electrode layer deposition, ceramic layer deposition, ceramic layer drying, and ceramic layer sintering are repeated alternatively until the desired number of layers has been formed. In a second method, which is preferred, the steps of electrode layer deposition, ceramic layer deposition, and ceramic layer drying are repeated until the desired layers have been formed and then the sintering step is executed to density all the ceramic layers. It is noted that the later method of preparing multilayer component is advantageously carried out faster and with less energy requirement.

It is also noted that this invention enables the sintering step to be carried out at lower temperatures and faster than the corresponding step of prior-art methods and at temperatures as low as 850 C because of the much greater diffusivity of nanosize particles in comparison to conventionally used materials, as mentioned above. Therefore, production savings result from lower operating temperatures, which require less energy input and less equipment insulation. Most importantly and advantageously, the lower sintering temperature permits the use of electrode compositions with lower melting points, such as those containing larger concentrations of silver or even pure silver, which is less expensive and a better conductor than the metals and alloys (e.g., of Pd and Pt) heretofore used as a result of the high temperature requirements of the sintering step of prior-art processes.

Finally, it is noted that the process of the invention can be readily used to prepare arrays of passive components—that is, devices with multiple passive components codeposited in series or parallel of each other in a single package.

Preparing Nanostructured Devices

As defined in the art, submicron powders are materials having average grain size below 1 micrometer. Of critical interest for this invention are nanoscale powders and nanostructured layers of ceramics and electrodes. Nanoscale powders (nanopowders) are submicron powders with average grain size less than 100 nanometers (preferably with a standard deviation of less than about 25 nm) and with a significant fraction of interfacial atoms. Accordingly, reference to nanoscale powders in this disclosure is intended to refer to powders with those characteristics.

Submicron layers are layers having thickness less than 1 micrometer. Of particular interest to this invention are nanostructured layers which are defined specifically as layers with thickness, or microstructure, or both, confined to a size less than property confinement size (positively less than 1 micron, preferably below 100 nm). Accordingly, reference to nanostructured layers in this disclosure is also intended to refer to layers with those characteristics.

As discussed in the copending applications, it is known that within these size ranges a variety of confinement effects occur that dramatically change the properties of the material. The idea of this invention then is to build ion conducting solid electrolytes from powders whose grain size has been confined to dimensions less than 100 nanometers. The size confinement effects in nanometer scale can confine fundamental processes to band-gap and quantum confined states which in turn can dramatically change the properties and performance of the resulting solid electrolyte. This insight can be implemented as devices prepared with one dimensional quantum dot and nanocluster composite with the dot size less than 100 nm (preferably less than 10 nm), as quantum wires with diameter less than 100 nm (preferably less than 10 nm), as quantized and nanoscale films with film thickness less than 100 nm, as nanostructured layers and pellets with microstructure less than 100 nm, and as a combination of these. In summary, another aspect of the invention concerns the preparation of solid electrolyte and electrodes that are nanostructured.

Nanostructured ion conducting electrolytes prepared from nanostructured materials have grain sizes spatially confined to less than 100 nanometers; a significant fraction (20-60%) of their atoms is interfacial, and exceptional interactions occur between the constituent domains. Therefore, nanostructured oxygen-conducting electrolytes can be expected to have very high concentrations of interface area which can assist rapid and low-temperature densification of ion conducting electrolytes. The nanoscale powder can also enable dramatic reduction in layer thicknesses as discussed in co-pending applications. Furthermore, since nanostructure provides higher density of surface area, the density of triple points at the electrolyte-electrode-gas interface can also be significantly enhanced using nanostructured-electrolyte/ electrode interactions. Given low resistance and high triple-point concentration, nanostructured electrolytes and electrodes can be used to achieve higher ion conductivity and electrochemical activity. This is of particular interest when an ion conducting device has to operate at near ambient temperatures. This general design principle is applicable to all, solid ion conductors based on ion defect structure, two dimensional layered structure, three dimensional network structure, vitreous structure, α-AgI type structure, and composites prepared using these structures. Illustrative examples include, without limitation, oxide ion conductors such as stabilized zirconia, stabilized ceria, stabilized bismuth oxide, perovskites, LISICON, NASICON, and β-alumina.

The following examples illustrate different ways of reducing the present invention to practice.

1. EXAMPLE 1

A stock solution was prepared from $ZrOCl_2.8H_2O$ and 9 mol % $Y_2O_3$ in water, and diluted with denatured ethanol. The solution was chilled to 0° C. and then slowly added to a continuously stirred basic solution of ammonium hydroxide that was also maintained at 0° C. Precipitation of white precursor powder was instantaneous. The precipitate solution was suction filtered, and the gelatinous filter cake was washed in denatured ethanol three times. The loose powder so generated was dried quickly with mild heating at 100° C. to remove water and ethanol, and calcined to 500° C. in air to form nanocrystallites with grain size of about 5.8 nm, standard deviation of 1.1 nm. This precursor material consisting of 9 mole-percent yttria stabilized zirconia (YSZ)

nanoscale powders was examined using, an X-ray diffractometer (XRD). A typical XRD pattern for the 9 mole powders so produced is illustrated in FIG. 3, which shows that the $ZrO_2$ is stabilized cubic phase. In order to determine the average particle size of the powders, the widths of strong, low order peaks of XRD pattern were analyzed using Scherrer's method. The average particle size of the powders according to this analysis was found to be about 4.5 nanometers. The particle size was also verified by transmission electron microscopy (TEM). The results suggested a particle size of 5.8 nanometers.

The nanoscale 9 mole % yttria stabilized cubic zirconia powders were pressed into 3 mm diameter discs (0.15 gram weight) and sintered to high densities (preferably more than 90% of theoretical density for mechanical strength, over 95% being preferred). The sample disks were sintered at low temperatures (1,150 to 1,250° C., yielding more than 95% density) and for short duration (6 to 24 hours) to minimize grain growth. We found that YSZ nanopowders readily sintered to full theoretical densities at about 1,200° C. in 17 hours, which represent significantly milder and less expensive processing conditions than presently necessary. Careful control of the sintering profile and time can further reduce the sintering temperature and time. The cylindrical discs were examined under XRD and the post-sintered mean grain size by Scherrer analysis was found to be about 83 nm, confirming that the discs were nanostructured. The two ends of the cylindrical discs so produced were then coated with a cermet paste consisting of a mix of silver and nanoscale yttria stabilized zirconia powder (about a 50-50 wt % mix, corresponding to a 35Ag-65YSZ vol % mix). Then platinum leads were attached to the cermet layer.

Figure 5:
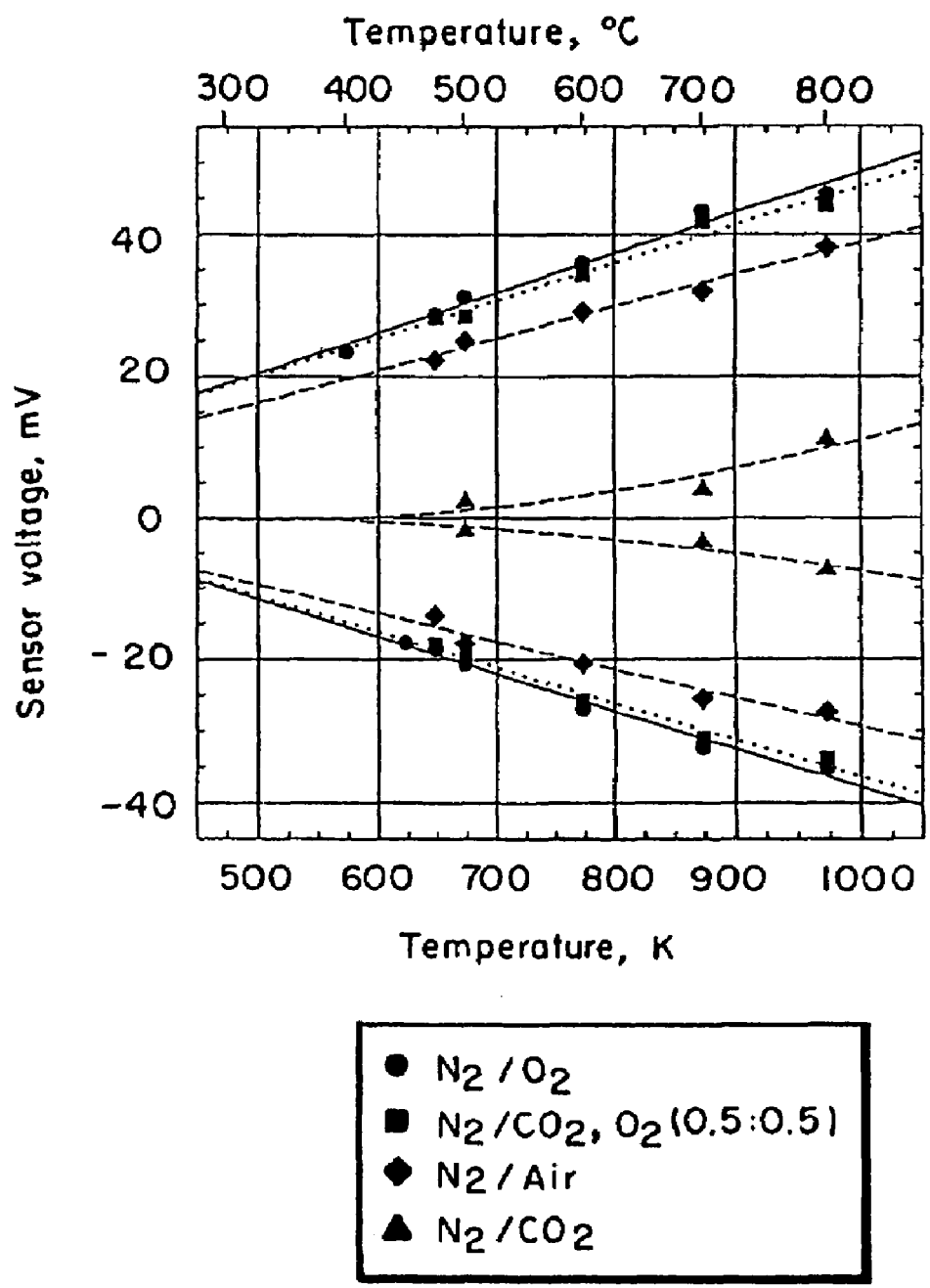
FIG. 5 is a voltage-versus-temperature graph of a nanostructured oxygen sensor manufactured with the material prepared in Example 1. The symmetrical response about the abscissa relates to switching the gases from one face of the sensor to the other.

The samples were placed in a furnace and their impedance was measured in air as a function of increasing temperature with a computerized impedance analyzer. A standard 40 mV AC bias and frequency sweep range of 5 Hz to 13 MHz were used. As illustrated in FIG. 5, the results so obtained suggest that nanostructured oxygen-conducting electrolytes, referenced by n, exhibit almost an order of magnitude higher oxygen-ion conductivities at lower temperatures when compared with base-line electrolytes, referenced by $\mu$ (i.e., conventional micron-powder based oxygen-conducting electrolytes). It is noted that neither the baseline nor the nanostructured electrolytes represent optimal performance. For additional electrochemical and electrocatalytic performance evaluation, the Ag/YSZ/Ag cell was tested as a sensor and oxygen pump. For sensor/fuel-cell experiments, oxygen containing gas was passed over one face of the sensor and nitrogen was passed over the other face of the sensor. The EMF response as a function of temperature was measured. As shown in FIG. 5, the results indicate that the sensor signal for each gas combination is linear with temperature, confirming a Nernst-type behavior. For electrosynthetic oxygen generation and pumping applications, $CO_2$ was passed over one face while nitrogen was passed over the other face. FIG. 5 shows that the oxygen-conducting electrolyte exhibited oxygen pumping properties at low temperatures.

2. EXAMPLE 2

Figure 6:
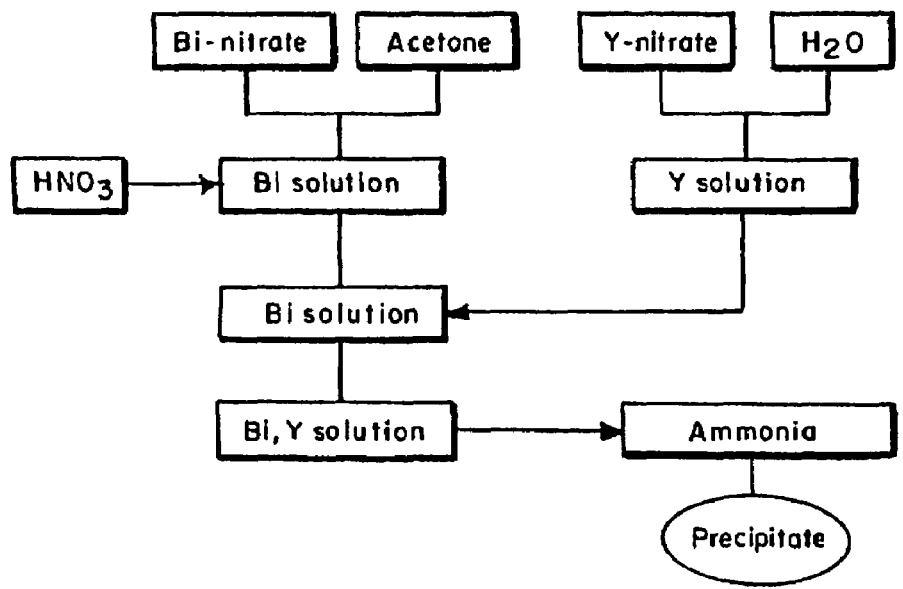
FIG. 6 is a flow chart of the process for preparing a yttria stabilized bismuth oxide (YSB) nanopowder from nitrates by a solution method.
Figure 7:
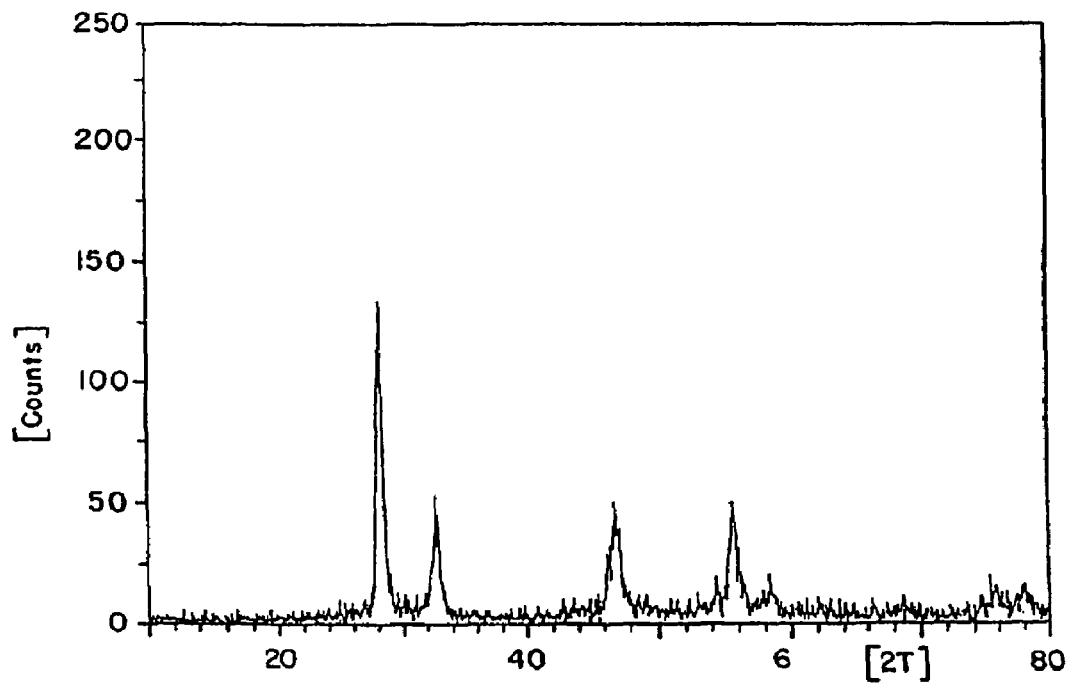
FIG. 7 is an X-ray diffraction pattern of the nanostructured YSB product of Example 2.

Bismuth nitrate $(Bi(NO_3)_3.5H_2O)$ and yttrium nitrate $(Y(NO_3).6H_2O)$, were as precursors for preparing nanosized yttria stabilized bismuth oxide (YSB) powder via solution co-precipitation. FIG. 6 shows a flow chart of the co-precipitation processing steps used in this example. After precipitation, the precipitate solution was suction filtered, and the gelatinous filter cake was washed in acetone to minimize agglomeration of ultrafine powder due to hydrogen bonding. The loose powder so generated was next dried with mild heating to remove water and acetone. Then the powder was calcined in air at 500° C. for 2 hours. XRD showed that calcine schedule resulted in a single cubic YSB phase (see FIG. 7). The volume averaged crystallite size of the powder fired at 500° C. was determined to be 12.5 nm by analyzing the broadening of the (111) diffraction peak and applying Scherrer's formula. The YSB nanopowder was characterized in terms of morphology and particle size by transmission electron microscopy (TEM). The average particle size was estimated to be about 15 nm, which is in good agreement with the result obtained from XRD analysis.

The nanopowders were uniaxially pressed at 50,000 psi into green pellets of 12.5 mm in diameter and 1 mm in thickness. The pressing process consisted of initially lubricating the die with a die lube, followed by the weighing of an appropriate amount of powder, inserting the powder in the die, uniaxially pressing to the desired pressure, holding at that pressure for 30 seconds, and then slowly releasing the pressure over 15 seconds. Subsequently, the pellet was forced out from the die. No binder was added for the forming, process. It was found that from the nanopowder the electrolytes can be sintered with greater than 96% of theoretical density at temperatures ranging from 850 to 950° C. In contrast, YSB electrolytes made from micron-sized powder are typically sintered at temperatures greater than 1,000° C. It is known that the primary driving force for densification of ceramics is the reduction of free surface area at high temperatures. The very small size of the YSB nanopowder, therefore, has a very large driving force for densification; thus, the required sintering temperature can be significantly reduced relative to commonly used micron-sized powders. This is an important manufacturing advantage of this invention.

The concept of the invention is also applicable to improve the performance of electrodes for ion conducting materials. These electrodes should have high electrical conductivities, high catalytic activities, adequate porosity for gas transport, good compatibility with the electrolyte, and long-term stability. In order to achieve high catalytic activities, it is preferred that the electrode be highly porous, so that it retains a large number of active sites for electrochemical reactions, i.e., the triple points. Ag has been studied as an electrode material because it is known to have high electrical conductivity and high catalytic activity for oxygen reduction and evolution. However, pure Ag electrodes readily densify during processing and operation, resulting in a dense electrode with little porosity. In order to reduce the electrode resistance, the teachings of this invention were used to prepare nanocomposite electrodes from Ag and nanostructured powders of the ion electrolyte material.

3. EXAMPLE 3

YSB electrolyte pellets, 19 mm in diameter and 0.9 mm in thickness, were sintered from green pellets of 25 mm in diameter and 1.2 mm in thickness. The pellets were ground and polished to a thickness of 0.7 mm to provide a suitable electrolyte substrate. A separate composite paste of 79 vol % Ag and 21 vol % YSB was prepared by mixing nanopowder of YSB and unfritted Ag paste (marketed by the Cermalloy Division of Heraeus Incorporated of West Conshohocken, Pa., under Catalog No. C440OUF). The paste was printed onto both sides of the pellet to form electrodes, and then the pellet was fired at 800° C. for 10 minutes to sinter the electrolyte without densifying it beyond the point necessary to provide a robust structure and form a stabilized sensor cell with porous composite electrodes (about 18% porosity). Then Ag wire was attached to both electrodes with a contact of Ag epoxy which was fired at 730° C. for 2 minutes. It is noted that the composite-electrode/electrolyte structure needs to be stabilized by the application of heat, pressure or chemical action, as the particular composition of the composite constituents may require or allow, in order to provide a physically robust and stable product.

In the resulting composite electrode structure, we found that the densification of the Ag phase is inhibited by the ion electrolyte material phase. The electrodes then retain a porous microstructure during and after thermally demanding processing and operation. The retained porous microstructure significantly enhances the performance of the electrodes. In addition, electrodes of this kind have better adhesion to the electrolytes because the stress arising from thermal expansion mismatch between the ceramic electrolyte and the metal electrode is minimized not only by the porous, heterogeneous microstructure of the electrodes but also by tailoring the thermal expansion coefficient of the nanocomposites. We found that a nanostructured electrode composite sintered to 50-85 percent of full theoretical density (i.e., producing an electrode composite with 15-50 percent porosity) is optimal to obtain these advantages of performance.

Figure 8:
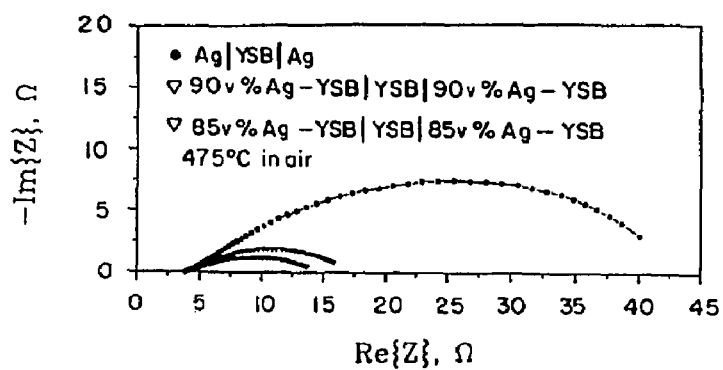
FIG. 8 illustrates Nyquist plots of impedance spectra of cells with the nanocomposite electrodes of Example 3 in comparison with a cell with pure Ag electrodes.

Further, another important advantage is derived from using nanocomposite electrodes. If the phases added are ionic conductors or mixed electronic-ionic conductors, the nanocomposite electrode as a whole turns out to be a mixed conductor, which allows ambipolar transport within the solid phase. FIG. 8 illustrates Nyquist plots of impedance spectra of cells with the nanocomposite electrodes in comparison with a cell with pure Ag electrodes. As determined from the impedance spectra, the polarization resistances of the nanocomposite electrodes are significantly smaller than that of the pure Ag electrode. As expected, the resistance of the nanocomposite electrode is a function of the composition, i.e., the volume fraction of each constituent phase. This allows much room for performance optimization by adjusting the composition of the composites. The nanocomposite electrode shows a nearly 4-fold reduction in electrode resistance as compared to the pure Ag electrode. We found that good results are obtained with a mix of 0 to about 65 vol % electrolyte (35 to 100 vol % metallic electrode material), the limit being that a continuum metal phase must exist for a viable porous electrode structure. That is, the amount of electrolyte must not be so great as to cause interruptions in the connectivity of the metal phase. At least 5 vol % electrolyte, 21 vol % being preferred, produced good results with different metal/electrolyte combinations. We believe that with composition optimization, further reduction in electrode resistance can be achieved, leading to a significant enhancement in ion conducting device's performance.

A sensor produced with the structure manufactured in Example 3 was operated in the following configuration, using air as the reference gas:

air, 79 v % Ag21 v % YSB|YSB|79 v % Ag21 v % YSB, Analyte gas.

The sensor response to the changes in the gas composition and in temperature was monitored by measuring the cell voltage under different conditions.

Figure 9:
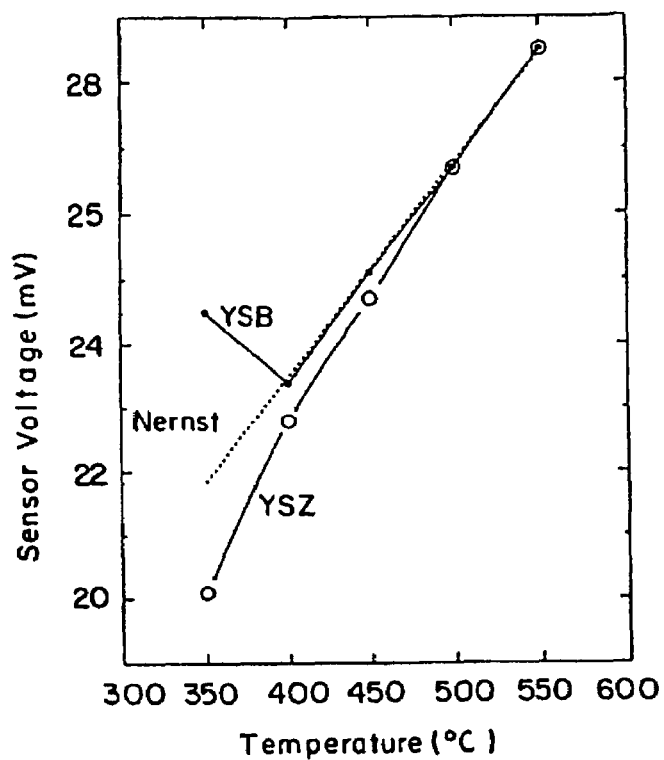
FIG. 9 is the voltage response in oxygen of the sensor of Example 3 as a function of temperature in comparison with that of a conventional YSZ sensor.

Shown in FIG. 9 is the sensor voltage response in oxygen as a function of temperature in comparison with that of a conventional YSZ sensor. FIG. 9 clearly shows that the response of the YSB sensor follows Nernst behavior down to 400° C., while the response of the YSZ sensor deviates from Nernst behavior below 500° C. This indicates that the YSB proof-of-concept sensor can be operated at a temperature about 100° C. lower than conventional YSZ sensors.

Figure 10:
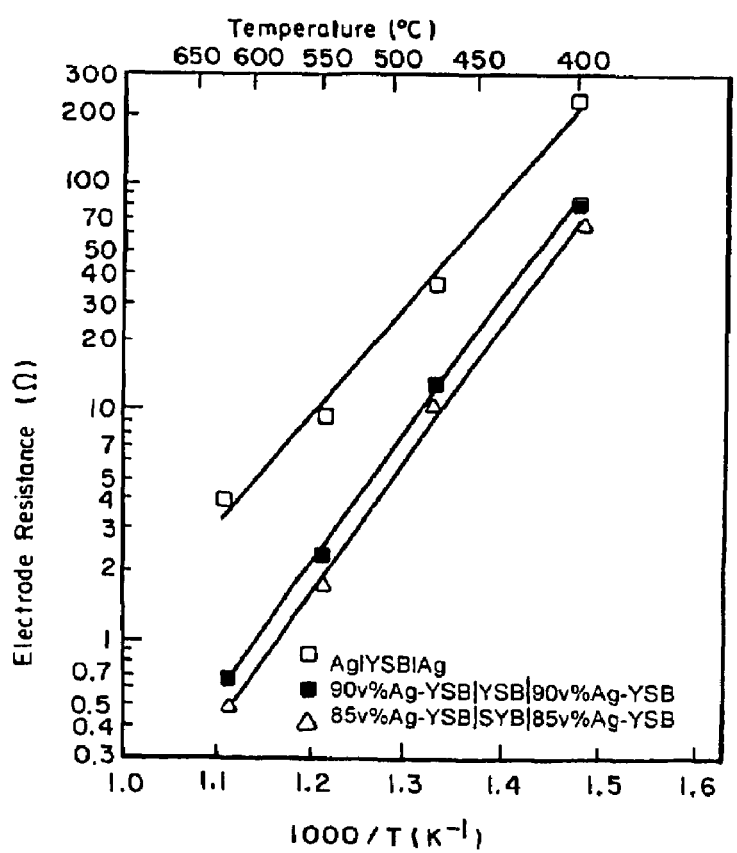
FIG. 10 shows electrode resistances of pure Ag electrode and nanocomposite electrodes as a function of temperature, as determined from the impedance spectra measured in air.
Figure 11:
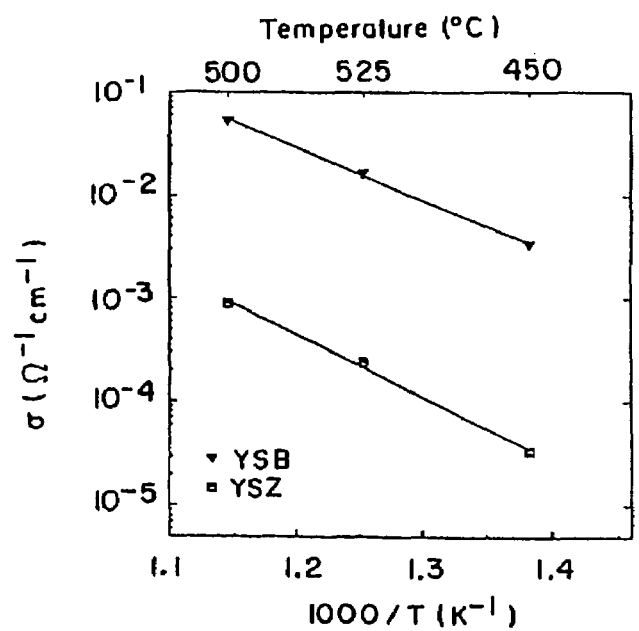
FIG. 11 shows a comparison of the ionic conductivity of nanostructured YSB electrolyte with YSZ electrolyte.

FIG. 10 further shows electrode resistances of nanocomposite electrodes as a function of temperature, as determined from the impedance spectra measured in air. Also shown in the figure are the data for pure Ag electrode for comparison. As compared with pure Ag electrode, the nanocomposite electrodes show significantly lower resistances. The ionic conductivity of the nanostructured YSB electrolyte was measured and found to be over two orders of magnitude higher than that of YSZ electrolyte, as shown in FIG. 11.

Figure 12:
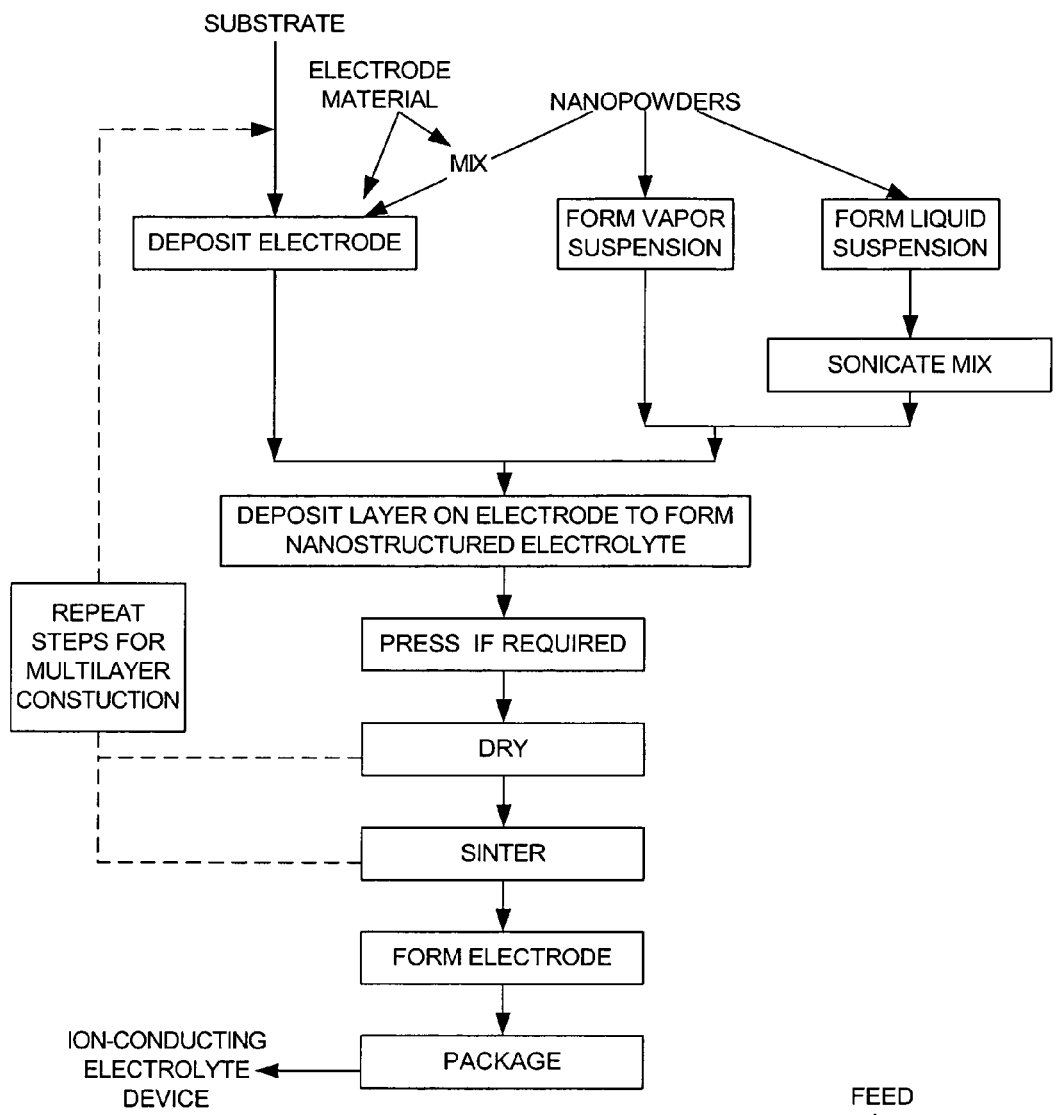
FIG. 12 is a flow diagram of the steps of deposition over a supporting substrate according to known vapor deposition processes applicable to the manufacture of nanostructured electrolytes according to the invention.

The impedance measurements and the data shown in these examples establish that nanostructured solid ion electrolytes and electrodes are indeed significantly superior in performance to solid ion electrolytes and electrodes prepared from micron-sized powders. The invention reduced to practice the use of nanostructured ion-conducting electrolytes exhibiting ion conductivity higher than obtained by prior-art technology; and it demonstrated the successful fabrication of ion-conducting electrolytes in general, and oxygen-conducting electrolytes in particular, from materials with grain size less than 100 nm for electrochemical, electrosynthesis and electrocatalytic applications. It is noted that the methods of assembly or deposition of nanoparticles to form structures according to this invention may vary depending on the particular application. For example, dry particles may be pressed into a structure of predetermined geometry, as illustrated in Example 1, or deposited over a supporting substrate according to known vapor deposition processes, as described in copending Ser. No. 08/730,661 and illustrated in FIG. 12.

4. EXAMPLE 4

Zinc

Commercially available zinc powder (−325 mesh) was used as the precursor to produce nanosize zinc powder. Feed zinc powder was fed into the thermal reactor suspended in an argon stream (argon was used as the plasma gas; the total argon flow rate was 2.5 ft$^3$/min). The reactor was heated with 16 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. The nanosize powder produced by the invention were in the 5-25 nanometer range. The size distribution was narrow, with a mean size of approximately 15 nm and a standard deviation of about 7.5 nm.

5. EXAMPLE 5

Iron-Titanium Intermetallic 2-5 micron powders of iron and 10-25 micron powders of titanium were mixed in 1:1 molar ratio and fed into the thermal reactor suspended in an argon stream (total gas flow rate, including plasma gas, was 2.75 ft³/min). The reactor was heated with 18 kW of plasma to over 5,000K in the plasma zone and above 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. The nanopowders produced by the invention were in the 10-45 nanometer range. The size distribution was narrow, with a mean size of approximately 32 nm and a standard deviation of about 13.3 nm.

6. EXAMPLE 6

Tungsten Oxide

Commercially available tungsten oxide powder (−325 mesh size) was used as the precursor to produce nanosize $WO_3$. The tungsten oxide powder was suspended in a mixture of argon and oxygen as the feed stream (flow rates were 2.25 ft³/min for argon and 0.25 ft.sup.3/min for oxygen). The reactor was heated with 18 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. The powder produced by the invention were in the 10-25 nanometer range. The size distribution was narrow, with a mean size of about 16.1 nm and a standard deviation of about 6.3 nm.

7. EXAMPLE 7

Cerium Oxide

Commercially available cerium oxide powder (5-10 micron size) was used as the precursor to produce nanosize $CeO_2$. The cerium oxide powder was suspended in a mixture of argon and oxygen as the feed stream (at total rates of 2.25 ft³/min for argon and 0.25 ft³/min for oxygen). The reactor was heated with 18 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 650 Torr. The powder produced was separated from the gas by means of a cooled copper-coil-based impact filter followed by a screen filter. The powder produced by the invention was in the 5-25 nanometer range. The size distribution was narrow, with a mean size of about 18.6 nm and a standard deviation of about 5.8 nm.

8. EXAMPLE 8

Silicon Carbide

Commercially available silicon carbide powder (−325 mesh size) was used as the precursor to produce nanosize SiC. The powder was suspended in argon as the feed stream (total argon flow rate of 2.5 ft³/min). The reactor was heated with 18 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. The SiC powder produced by the invention were in the 10-40 nanometer range. The size distribution was narrow, with a mean size of approximately 28 nm and a standard deviation of about 8.4 nm.

9. EXAMPLE 9

Molybdenum Nitride

Commercially available molybdenum oxide ($MoO_3$) powder (−325 mesh size) was used as the precursor to produce nanosize $Mo_2N$. Argon was used as the plasma gas at a feed rate of 2.5 ft³/min. A mixture of ammonia and hydrogen was used as the reactant gases ($NH_3$ at 0.1 ft³/min; $H_2$ at 0.1 ft³/min). The reactor was heated with 18 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. The $Mo_2N$ powder produced by the invention was in the 5-30 nanometer range. The size distribution was narrow, with a mean size of about 14 nm and a standard deviation of about 4.6 nm.

10. EXAMPLE 10

Nickel Boride 10-50 micron powder of nickel boride were fed into the thermal reactor with argon (fed at a total rate, including plasma gas, of 2.75 ft³/min). Once again, the reactor was heated with 18 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. The $Ni_3B$ powder produced by the invention was in the 10 to 30 nanometer range. The size distribution was narrow, with a mean size of about 12.8 nm and a standard deviation of about 4.2 nm.

11. EXAMPLE 11

Reacting Feed

Oxide Ceramics: 5-10 micron powders of calcium carbonate were fed into the thermal reactor with argon (at 2.5 ft³/min). The reactor was heated with 16 kW of plasma to over 5,000K in the plasma zone and about 2,500K in the extended reactor zone adjacent the converging portion of the nozzle. The vaporized stream was quenched by thermal expansion to about 100 Torr. The pressure drop across the nozzle was 250 Torr, but useful results were obtained at different pressure drops, ranging from 50 to 550 Torr. The powder produced was separated from the gas by means of a cooled copper-coil-based impact filter followed by a screen filter. The TEM image of powder produced show it to be in the 5 to 20 nanometer range. As expected from the reaction occurring in the reactor, the XRD data established that the main phase of the nanopowder was CaO. The size distribution of the CaO was narrow, with a mean size of about 14.8 nm and standard deviation of about 3.8 nm.

An alternate run was made with $MgCO_3$ powders with mean size of about 7 microns processed with argon. Once again, nanoscale powders of MgO were produced as evidenced by TEM and XRD data. The final product powder size was observed to vary with changes in the pressure, temperature, flow rate, and compositions.

12. EXAMPLE 12

Capacitor $TiO_2$ nanopowders were synthesized by chemical precipitation of $TiCl_4$. The aqueous chloride solution was cooled and maintained at 0° C. and precipitated by adding 7M $NH_4OH$ under rapid stirring. The precipitates were then filtered and calcined in air for one hour at 400° C. The nanopowders produced were characterized using TEM, XRD, and BET adsorption equipment. The mean size of the nanopowder, as determined by TEM was 13.9 nm, with a standard deviation, as determined by TEM, of 4.4 nm. The phase, as determined by XRD, was found to be anatase $TiO_2$; and the surface area as determined by BET was 66.7 $m^2$/gm. The nanopowders were suspended in denatured alcohol with 1 wt % polyethylene glycol binder for preparing the dielectric layer.

Single crystal Si wafers (½"×½") were used as substrates for mechanical support. The substrate was first coated with a thin layer of Pd/Ag alloy (about 500 nm in thickness) using plasma sputtering, and then coated with a thin film of $TiO_2$ as follows.

The nanopowder suspension in denatured alcohol was stirred and then the substrate was dipped into the suspension and removed. The uniform ultra-thin $TiO_2$ film on the Si substrate was dried and sintered in air. The drying was first done in air at room temperature for 30 minutes and then in a furnace at 150° C. for 30 minutes. The densification was done in the furnace at 850° C. for 2 hours. The resulting surface of the $TiO_2$ layer was further coated with a Pd/Ag layer (about 500 nm in thickness and 5 mm in diameter) to produce an ultra-thin $TiO_2$ capacitor on a silicon substrate.

In order to characterize the TiO2-coated substrate, the wafers were fractured and their cross sections were observed under a Hitachi field emission scanning electron microscope (SEM model S-4500). The samples were not coated with conductive Au during SEM in order to avoid any possible cover-up of nanostructure details by coated Au films. The microstructure of the TiO2 film was as small as 100 nm.

The dielectric properties of these ultrathin dielectric capacitors were evaluated using an HP 4274A Multi-frequency LCR meter, a Ransco Thermal Cycler (for capacitance measurements), and a Keithley 246 high voltage supply (for breakdown voltage measurements). The capacitance measurements were conducted at different temperatures from 30° C. to 130° C. with a frequency of 1 kHz. The dielectric constant so determined was 89.2. The dissipation factor was less than 5%, while the dielectric strength of the nanostructured layer was observed to be 220 Volts/micrometer. The temperature coefficient of capacitance was found to be less than 1%. Compared to a micron powder based 20 micron dielectric layer capacitor, the capacitor prepared from nanoscale, interface confined powders was found to enhance volumetric efficiency by 100 fold, and energy density by more than 2000 fold.

Nanostructured dielectric layer capacitors prepared from directly precipitating nanostructured layer on silicon wafer from a solution of titanium alkoxides in a moist environment using spin coating apparatus also exhibited statistically similar performance.

Nanostructured capacitors prepared from nanopowders produced by other processes, such as the method disclosed in the referenced copending applications, exhibited statistically similar performance, as illustrated below.

13. EXAMPLE 13

Capacitor

Single crystal Si wafers (½"×½") were again used as substrates for mechanical support. The substrate was first coated with a thin layer of Pd (about 500 nm in thickness) using plasma sputtering, and then coated with a thin film of $TiO_2$ as follows.

A suspension was made from nano-$TiO_2$ powder with average grain diameter of 20 nm and a standard deviation of about 2.8. A polyethylene glycol binder and ethanol solvent were used. The suspension was stirred for 24 hours before coating. The dip coating method was used to prepare uniform ultra-thin $TiO_2$ films on the Si substrates. The film was dried and sintered in air. The drying was first done in air at room temperature for 30 minutes and then in a furnace at 150° C. for 30 minutes. The densification was done in the furnace at 850° C. for 2 hours. The resulting surface of the $TiO_2$ layer was further coated with a Pd layer (about 500 nm in thickness and 5 mm in diameter) to produce an ultra-thin $TiO_2$ capacitor on a silicon substrate.

In order to characterize the $TiO_2$ coated substrate, the wafers were fractured and their cross sections were observed under a Hitachi field emission scanning electron microscope (SEM model S-4500). The samples were again not coated with conductive Au during SEM in order to avoid any possible cover-up of nanostructure details by coated Au films. The $TiO_2$ film in this case was about 850 nm in thickness. The microstructure of the $TiO_2$ film was as small as 100 nm.

The dielectric properties of these ultrathin dielectric capacitors were also evaluated using an HP 4274A Multi-frequency LCR meter, a Ransco Thermal Cycler (for capacitance measurements), and a Keithley 246 High Voltage Supply (for breakdown voltage measurements). The capacitance measurements were conducted at different temperatures from 30° C. to 130° C. with a frequency of 1 kHz. The measured dielectric properties of this ultra-thin $TiO_2$ capacitor are listed in Table 1 below.

TABLE 1

| | |
|---|---|
| Dielectric Thickness (μm) | 1.67 μm |
| Electrode area ($mm^2$) | 19.625 |
| Capacitance @ 25° C. (nF) | 9.28 |
| Dielectric Constant @ 25° C. | 9.2 |

TABLE 1-continued

| | |
|---|---|
| Dissipation factor (%) | 5.0 |
| Dielectric Strength (V/μm) | 220 |

The volumetric efficiencies of base capacitors (20 and 100 μm in thickness) and of ultra-thin TiO2 capacitors (2 μm in thickness) were calculated for comparison according to equation (1). The results are listed in Table 2 below.

TABLE 2

| Capacitors | Base case L = 100 μm | Base case L = 20 μm | Nanoceramic L = 2 μm |
|---|---|---|---|
| C/v (nF/cm³) | 0.078 | 1.77 | 177 |

The data in Table 2 show that, compared to the base case where the thickness was 20 μm, the nanostructured $TiO_2$ capacitor enhanced the volumetric efficiency by 100 times. Compared to the base case where the thickness was 100 μm, the nanostructured $TiO_2$ capacitor enhanced the volumetric efficiency by over 2,200 times.

The energy densities of base capacitors (20 and 100 μm in thickness) and nanostructured $TiO_2$ capacitors (2 μm in thickness) were also calculated according to equation (2). The calculated results are listed in Table 3 which shows that, compared to the base case where the thickness is 20 μm, a nanostructured $TiO_2$ capacitor 2 μm thick would raise the energy density of the dielectric layer by 100 times. Compared to the base case where the thickness is 100 μm, the nanostructured $TiO_2$ capacitor would raise the energy density of the dielectric layer by about 2,500 times.

TABLE 3

| Capacitors | Base case L = 100 μm | Base case L = 20 μm | Nanoceramic L = 2 μm |
|---|---|---|---|
| E/m (J/kg) | $2.13 \times 10^{-2}$ | $5.32 \times 10^{-1}$ | 53.2 |
| E/m (w · hr/kg) | $5.92 \times 10^{-6}$ | $1.48 \times 10^{-4}$ | $1.48 \times 10^{-2}$ |

These examples demonstrate that capacitors can be prepared from dielectric powders with mean size less than 100 nanometers resulting in capacitor dielectric layers with post-densification grain size of less than 1 micron. The examples also illustrate a procedure for preparing micron and submicron layers of electrical and electronic ceramics sandwiched between electrically conducting electrodes and for preparing ceramic capacitors at processing temperatures low enough that pure silver can be used as the electrode material instead of expensive alloys of silver.

While silver alone was not used as electrode material because of availability, the low sintering temperature of 850° C. supports the premise that silver can be used as electrode for nanostructured layer capacitors.

Based on these results, it is anticipated that multilayer ceramic capacitors can be similarly fabricated. Ultra-thin (about 400 nm) dielectric layers 32 can be packed into the minimum possible space in a mechanically robust form. The typical inter-electrode spacing can be about 400 nm, which is more than 25 times thinner than what the best current technology can achieve. Thus, 50 to 100 layers can be stacked in a small volume. The process involves the following major steps: preparing the ceramic solution, making ultra-thin layers, preparing electrodes, dicing into chips, firing (densification), making terminations and testing.

Thus, the invention demonstrated that very high energy density and very high power density multilayered capacitors can be fabricated from nanostructured ceramic dielectrics, i.e., monosize ceramic dielectric powders with mean particle size in the $10^{-1}$ to $10^{-3}$ Φm range. Through the use of nanoceramics, the invention achieved a reduction of the dielectric layer thickness by more than an order of magnitude, thereby providing a commensurate degree of miniaturization and enhancing the capacitance and energy density of same size multilayered capacitors by a factor of up to $10^6$. It showed the possibility of dramatically lowering the ESR of multilayered capacitors, with consequent increase in power density by several orders of magnitude. Although experimental data suggest that the dielectric constant of materials first decreases as the grain size becomes smaller, the use of nanostructured materials confirmed the fact that beyond a critical diameter (smaller than 1 Φm) the dielectric properties enter a different phenomenological regime and reductions in grain size significantly enhance the dielectric constant. Nanoceramics are superplastic (very ductile) at relatively moderate temperatures and therefore can produce ultra-thin plates of dielectric more easily and without the use of binders, which reduces impurity contamination. The enhanced creep rates in nanoceramics can allow for low temperature (less than 950° C.) sintering of the nanostructured film to produce a defect-free, full density dielectric layers. An additional advantage of the low-temperature sintering characteristics of nanoceramics is the replacement of expensive Ag/Pd alloys with Ag as the electrode layer material. Moreover, experimental data suggest that nanoceramics are stronger and harder, by more than 500%, than bulk ceramics, which implies that nanostructured capacitors would be mechanically robust even after reduction of the dielectric layers' thickness. Nanoceramics, because of their nanoscale sizes, can lead to a homogeneous mixing of K-modifiers and additives to near-theoretical levels. This should enable the creation of multilayered capacitors and other passive electronic components with very low performance spread. Inasmuch as it has been suggested that nanostructured ceramics should feature a lower coefficient of thermal expansion than their larger precursors, the temperature coefficient of nanostructure components should be lower than that of existing components. Similarly, the lower temperature coefficient of capacitance of nanostructured capacitors should enable their use in applications requiring a broader temperature range (e.g., for dual-use applications such as hybrid or electric vehicles where under-hood temperatures can reach 150° C.). It is expected that the performance of passive electronic components can be improved for operation at higher frequencies and that nanostructured components may be engineered with unique combinations of properties that have been heretofore unavailable.

From a commercial point of view, the approach of this invention is also very desirable because it does not require novel chemistries or components whose environmental and ecological impact is unknown. The approach also avoids the pit-fall common to competitive technologies that ignore raw material availability and source issues, scale up issues, manufacturing equipment availability, and labor training issues. Powder processing has been practiced by the passive component industry for decades. Therefore, the approach of this invention blends well with current reality and builds on it by exploring, developing and implementing the knowledge of precision engineering to the art. Nanopowders, therefore, are an extraordinary opportunity for design, development and commercialization of a wide range of structural, electrochemical, electrical, optical, electronics, magnetic and chemical applications. Furthermore, since nanopowders represent a whole new family of precision engineered material precursors where conventional coarse-grain physiochemical mechanisms are not applicable, nanomaterials offer unique combinations of properties that may enable novel and multifunctional components of unmatched performance.

14. EXAMPLE 14

Varistors

Nanoscale powders of zinc oxide were obtained as follows in order to manufacture varistors according to the invention. Zinc carbonate was precipitated by mixing solutions of zinc nitrate and ammonium carbonate in equal molar ratio. Specifically, a 0.1 molar solution of $Zn(NO_3)_2$ was prepared by dissolving 29.747 g of the salt in distilled water. Approximately 0.1M $(NH_4)_2CO_3$ was prepared by dissolving 11.34 g of ammonium carbonate (assay $\geq$30%) in distilled water. On hundred ml of 0.1M $Zn(NO_3)_2$ solution was added slowly into a stirred solution of 100 ml of 0.1M $(NH_4)_2CO_3$. Precipitation occurred immediately. After stirring for more than one half hour, the precipitate was filtered using a buchner funnel fitted with a fritted disc (ASTM 10-15 μm) by vacuum suction. The precipitate was washed with water twice and then washed with ethanol. The precipitate was dried in air and then at 70° C. The powder obtained was ground thoroughly using agate or alumina mortar and pestle and calcined between 200 and 300° C. for 2 hours. The calcined powder was characterized by XRD, TEM and BET adsorption. The powder was nanoscale ZnO with typical sizes in the range of 5 to 20 nm. The mean size of the nanopowder, as determined by TEM, was found to be 11.2 nm with a standard deviation of 3.4 nm; the phase, as determined by XRD, was hexagonal ZnO, and the surface area as determined by BET was 55.8 m2/gm. The nanopowders were suspended in denatured alcohol.

According to the invention, nanoscale $Sb_2O_3$ (1 wt %), $Bi(NO_3)_3 \cdot 5H_2O$ (1 wt %), $Ni(NO_3)_2 \cdot 6H_2O$ (1 wt %), $Co(NO_3)_2 \cdot 6H_2O$ (0.5 wt %), $Mn(NO_3)_2 \cdot xH2O$ (0.5 wt %), $Al(NO_3)_3 \cdot 9H_2O$ (0.001 wt %) and $Cr(NO_3)_3 \cdot 9H_2O$ (0.1 wt %) were mixed ZnO powders (95.9 wt %) and reacted at 400° C. for 0.5 hours, and then at 300° C. for 1.5 hours. The nanocomposite powders were uniaxially pressed in a steel die at 20,000-30,000 psi. The discs were sintered in air at various temperatures for 1 to 2 hours. Sintered discs were given electrical contacts by printing silver paste on the opposite faces of the pellets. Platinum lead wires were attached to the silver paste. The silver paste was then dried by heating in an air oven at 80-100° C. for 1 hour.

Varistors so obtained were characterized for voltage-current behavior using a Keithley 2400 Source Meter. The nominal breakdown voltage (Vnom) and alpha (α) were determined from the data so obtained from the equation:

$$\alpha = \log(I_2/I_1)/\log(V_2/V_1) \quad (10)$$

where $V_1$ and $V_2$ are the voltages across the varistor at two test currents $I_1$ and $I_2$ in the non-linear region of the V-I characteristic. The nominal varistor (or breakdown) voltage, Vnom, is the varistor peak terminal voltage measured with a specified DC current applied (normally 1 mA for a corresponding varistor terminal voltage $V_{1\ mA}$).

For varistors discs that were sintered at 850° C. for one hour, an a of 19.5 and a $V_{nom}$ of 429 V/mm (at I=0.1 mA/cm$^2$) were observed. For varistor discs that were sintered at 1200° C. for one hour, an α of 30 and a $V_{nom}$ of 23 V/mm (at=1.9 mA/cm$^2$) were observed.

15. EXAMPLE 15

Resistors

Resistors were prepared according to the invention from nanoscale $SnO_2$ powders. An 85% $SnCl_4$ (wt %) aqueous solution was kept at 0° C. and precipitated by adding 14% $NH_4OH$ (wt %) with rapid stirring. The precipitate was filtered and washed with deionized water at 0° C. The powder was then dried at 100° C. for 60 minutes, ground, and calcined at 500° C. for 15 minutes. The nanopowder produced was characterized using TEM, XRD, and BET adsorption equipment. The Scherrer's grain size estimated from peak broadening of the XRD data was 4.1 nm. The specific surface area obtained from BET measurement was 97.7 m$^2$/g. The TEM micrograph indicated that the particle size and distribution were 9.1 nm with a standard deviation was 6 nm, and that the particle shape was round and irregular. EDS data showed strong Sn peaks and no other impurity.

A resistor was prepared from the nanopowder as follows. A high-temperature C4740S silver conductor paste (from Heracus Inc. of West Conshohocken, Pa.) was used to fabricate the electrode. The silver paste was painted on an alumina substrate, and air-dried for 15 minutes at 150° C.; the element was then stabilized at 850° C. for 10 minutes to provide conducting electrode layers that strongly adhered to the substrate. Nanosized $SnO_2$ was suspended in ethanol and dried to form a paste. The nanopowder paste was painted between electrodes. After air-drying, the binder solution (a silicate solution with a volume ratio of tetraethyl orthosilicate/ethanol/water/2% HCl of 65/27/7/1) was painted on the $SnO_2$ layer and allowed to permeate the $SnO_2$ layer. The element was air-dried and sintered at 450° C. for 30 min.

The nanostructured $SnO_2$ ceramic film was characterized by scanning electron microscopy and XRD. The XRD data confirmed the phase and the fact that the ceramic film was $SnO_2$. The Scherrer's post-sintering grain size was estimated from peak broadening of the XRD data to be 4.9 nm. The SEM image of the nanostructured $SnO_2$ film indicated that the microstructure of the film was extremely porous, that feature size of the $SnO_2$ cluster was about 20-30 nm, and that each of the $SnO_2$ clusters consisted of several extremely fine $SnO_2$ particles.

A Keithley model 2400 SourceMeter was used to determine the electrical behavior of synthesized $SnO_2$ thin films. Using a software application developed with Test Point 2.0, a standard characterization routine was performed for thin resistor film prototypes. Four-point probe leads were attached to each of the silver-painted electrodes, and the circuit was tested by measuring the film resistance at 21 volts (dc). Using the Test Point application Software, a voltage ramp of 0 to 35 volts (DC) was programmed to execute with a step size of 0.5 volts. The current through the film was measured at each voltage step and data were sent to a Microsoft Excel spreadsheet. The resulting current and voltage data were plotted against each other, and the slope of the line was used to calculate the resistance of each thin film using Ohm's law R=V/I. A plot of the V-I behavior for a typical thin film sample a linear relationship and a calculated DC resistance of about 9 megaohms. Background scans of the alumina substrate were also performed to ensure that all resistance effects noted were from the $SnO_2$ film.

AC impedance measurements of $SnO_2$ films were performed with a Solartron 1250 impedance/gain analyzer and Z60W analysis software. Probe lines were connected to the silver electrodes of the $SnO_2$ films and an AC resistance of 10 megaohm was observed at a frequency of 1000 Hz.

16. EXAMPLE 16

Inductors

Inductors were made according to the invention from nanoscale ferrite and from micron-sized particles for comparison purposes. The nanopowders were produced by the thermal quench process disclosed in the referenced copending applications and had an average grain size of 45 nm, a standard deviation of 17.1 nm, and a surface area of 25.1 $m^2/g$, as determined by the XRD, TEM and BET adsorption data. The nanopowders so produced and conventional ferrite powders (for comparison purposes) were pressed into cylinders (diameter=0.5 cm and length=1 cm) by mixing 1.5 g of ferrite ($NiFe_2O_4$) with 5 wt % of acrylate binder and dispersing the mixture into a solvent ($EtOH:H_2O$=1:1-Vol.:Vol.). The mixture was then sonicated for 30 minutes and the solvent was allowed to evaporate in an oven. When the powders were completely dry, they were pressed into cylinders with a Carver hydraulic press at 90,000 psi. The nanopowder-based cylinders were then sintered at 820° C. for 4 hrs. Note that micron powders of ferrite could not be sintered at this temperature, but required sintering at 1200° C. for 4 hrs. The inductor was prepared by wrapping silver wire (diameter 0.5 mm) in a spiral fashion around the ferrite cylinders (inductor cores). The coil had 50 turns and a diameter of 5.66 mm for both the micron powder based inductor core and for the nanopowder based inductor core. The inductance of the samples was then measured from 30 Hz to 30000 Hz using a computer interfaced Solartron 1260 (Frequency/Gain-Phase Analyzer). The results indicate that the inductance of nanopowder-based cores is almost an order of magnitude higher than that of cores based on conventional micron-sized powders.

Thus, electrode/ceramic layers for passive electronic components with properties markedly superior to those exhibited from prior-art processes can be achieved when nanopowders are used and nanostructured layers are produced. In its broadest form, applicable to the manufacture of all electronic passive components, the invention can be described. The critical steps consist of the deposition of at least one ceramic layer from a nanopowder under conditions that will produce a nanostructured film. For multilayer devices, additional alternate layers of electrode and ceramic are deposited either before of after sintering of each layer, as indicated by the dotted lines in the figure's flow chart. These steps are the ones that produce the exceptional passive-electronic-component properties rendered possible by the invention.

The process of deposition may also be incorporated with the process of manufacture of the nanosize particles disclosed in the referenced copending applications. This method is preferred because it enables the continuous fabrication of product from raw material. A thermal reactor system is used to produce nanoscale powders by ultra-rapid thermal quench processing of high-temperature vapors through a boundary-layer converging-diverging nozzle. A gas suspension of the micron-sized material is continuously fed to a thermal reaction chamber and vaporized under conditions that minimize superheating and favor nucleation of the resulting vapor. The high temperature vapor is quenched by passing the vapor stream through the nozzle immediately after the initial nucleation stages, thereby rapidly quenching it through expansion at rates of at least 1000° C. per second, preferably greater than 1000000° C. per second, to block the continued growth of the nucleated particles and produce a nanosize powder suspension of narrow particle-size distribution. A gaseous boundary-layer stream is preferably also injected to form a blanket over the internal surface of the nozzle to prevent vapor condensation in the throat of the nozzle. A receiving substrate is placed in the diverging section of the nozzle to receive the nanoparticles produced in the quenched stream. Thus, a nanostructured layer of electrolyte material can be deposited directly as desired on the particular device being manufactured. As those skilled in the art would readily understand, the precise location of the substrate within the nozzle, the residence time, and other operating parameters could be manipulated to produce the physical structure desired for a particular application.

Potential applications of the invention include nanostructured solid electrolyte and electrode based devices for energy storage and generation such as, but not limiting to batteries, fuel cells, devices for thermodynamic property measurements; electrochemical sensors for monoatomic, diatomic and polyatomic gases such as, but not limiting to atomic oxygen found in atmosphere, diatoamic oxygen and ozone sensors; ion sensors; oxygen pumps; solid state chemical pumps; monitors for steam electrolyzers; measurement of dissolved oxygen in liquid metals; measurement of pH; electrocatalysis, electrosynthesis, catalytic membrane reactors, and high-temperature kinetic studies. Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

We claim:

1. A method for manufacturing a product comprising one or more passive electronic components, wherein the method comprises:
   providing ceramic nanopowders;
   suspending the nanopowders in a solvent thereby preparing a nanopowder dispersion or paste;
   forming a layer from the nanopowder dispersion or paste such that the average grain size of the nanopowder in the layer is equal to or less than 100 nanometers; and
   wherein the layer provides at least one passive electronic device function selected from the group consisting of capacitor, resistor, varistor and inductor; and
   processing the layer into one or more passive electronic components.

2. The method of claim 1 wherein the ceramic nanopowders comprise an oxide.

3. The method of claim 1 wherein the ceramic nanopowders composition comprises two or more metals.

4. The method of claim 1 wherein the dispersion or paste comprises a polymeric composition of matter.

5. The method of claim 1 wherein the product comprises an electrode and the layer is formed on the electrode.

6. The method of claim 1 wherein the layer is a nanocomposite.

7. The method of claim 1 wherein the product comprises a multilayer device.

8. The method of claim 1 wherein the product comprises a device array.

9. The method of claim 1 wherein the product comprises interconnects.

10. The method of claim 1 wherein the product comprises multiple layers.

11. The method of claim 1 wherein the layer comprises polymer.

12. The method of claim 1 wherein the layer has a thickness less than 1 micron.

13. The method of claim 5 wherein the electrode comprises Pt, Pd, Au, Ag, Cu or Ni.

14. A method for manufacturing a product comprising one or more device components, wherein the method comprises:
providing ceramic nanopowders;
dispersing the nanopowders in a solvent thereby preparing a nanopowder dispersion or paste;
forming a layer from the nanopowder dispersion or paste such that the average grain size of the nanopowder in the layer is equal to or less than 100 nanometers; and
wherein the layer provides at least one device function selected from the group consisting of electromagnetic coupling, thermistor, piezo-device, magnetic device and interconnect; and
processing the layer into one or more passive electronic device components.

15. A method for manufacturing a product comprising one or more device components, wherein the method comprises:
providing ceramic nanopowders;
dispersing the nanopowders in a solvent thereby preparing a nanopowder dispersion or paste;
forming a layer from the nanopowder dispersion or paste such that the average grain size of the nanopowder in the layer is equal to or less than 100 nanometers; and
wherein the layer provides at least one device function selected from the group consisting of photoelectric device, thermoelectric device, ion-conducting electrolyte, battery, fuel cell and sensor; and
processing the layer into one or more passive electronic device components.

16. A method for manufacturing a product comprising one or more device components, wherein the method comprises:
providing ceramic nanopowders;
dispersing the nanopowders in a solvent thereby preparing a nanopowder dispersion or paste;
forming a layer from the nanopowder dispersion or paste such that the average grain size of the nanopowder in the layer is equal to or less than 100 nanometers; and
wherein the layer provides at least one device function selected from the group consisting of optical device, magneto-optical device, biomedical device and membrane device; and
processing the layer into one or more passive electronic device components.

17. A product prepared using the method of claim 1.

18. A product prepared using the method of claim 14.

19. A product prepared using the method of claim 15.

20. A product prepared using the method of claim 16.

21. A method for manufacturing a product comprising one or more passive electronic components, wherein the method comprises:
providing ceramic nanopowders;
preparing a nanopowder dispersion or paste comprising the ceramic nanopowders;
forming a layer from the nanopowder dispersion or paste such that the average grain size of the nanopowder in the layer is equal to or less than 100 nanometers; and
wherein the layer provides at least one device function; and
processing the layer into one or more passive electronic components.

* * * * *